US008133485B2

(12) United States Patent
Levi-Schaffer et al.

(10) Patent No.: US 8,133,485 B2
(45) Date of Patent: Mar. 13, 2012

(54) BI-SPECIFIC COMPLEXES FOR TARGETING CELLS INVOLVED IN ALLERGIC-TYPE REACTIONS, COMPOSITIONS AND USES THEREOF

(75) Inventors: Francesca Levi-Schaffer, Jerusalem (IL); Ido Bachelet, Modiln (IL); Ariel Munitz, Jerusalem (IL); Lorenzo Moretta, Genoa (IT); Alessandro Moretta, Genoa (IT)

(73) Assignees: Yissum Research Development Company of the Hebrew University of Jerusalem, Jerusalem (IL); DIMES - Dipartimento do Medicina Sperimentale - Universita degli Studi di Genova, Genoa (IT)

( * ) Notice: Subject to any disclaimer, the term of this patent is extended or adjusted under 35 U.S.C. 154(b) by 876 days.

(21) Appl. No.: 10/594,926

(22) PCT Filed: Mar. 30, 2005

(86) PCT No.: PCT/IL2005/000358
§ 371 (c)(1),
(2), (4) Date: Apr. 30, 2008

(87) PCT Pub. No.: WO2005/095460
PCT Pub. Date: Oct. 13, 2005

(65) Prior Publication Data
US 2008/0219980 A1 Sep. 11, 2008

Related U.S. Application Data

(60) Provisional application No. 60/557,377, filed on Mar. 30, 2004.

(51) Int. Cl.
*A61K 39/395* (2006.01)
*A61K 39/00* (2006.01)

(52) U.S. Cl. ............ 424/130.1; 424/133.1; 424/136.1

(58) Field of Classification Search .......... None
See application file for complete search history.

(56) References Cited

OTHER PUBLICATIONS

Lerner et al. 'Tapping the immunological repertoire to produce antibodies of predetermined specificity.' 299:592-596, 1982.*
Bachelet et al. 'Suppression of normal and malignant kit signaling by a bispecific antibody linking Kit with CD300a.' J. Immunol. 180:6064-6069, 2008.*
Bachelet et al. 'Abrogation of allergic reactions by a bispecific antibody fragment linking IgE to CD300a.' Allergy. 117:1314-1320, 2006.*
Munitz et al. 'Inhibitory receptors on eosinophils: A direct hit to a possible Achilles heel?' J. Allergy. Clin. Immunol. 119:1382-1387, 2007.*
Munitz et al. 'Reversal of airway inflammation and remodeling in asthma by a bispecific antibody fragment linking CCR3 to CD300a.'J. Allergy Clin. Immunol. 118(5):1082-9, 2006.*
Chemicon International Rat Anti-Mouse CD117 Biotin-Conjugated Monoclonal Antibody Product description, p. 1, May 2005.*
Millipore POFlowCellect™ Chemokine Receptor CCR3 Surface Expression Identification ki Product Description, pp. 1-13, Aug. 2008.*
Translation of Notice of Reason for Rejection Dated Oct. 25, 2011 From the Japanese Patent Office Re. Application No. 2007-505735.

* cited by examiner

*Primary Examiner* — Nora Rooney

(57) ABSTRACT

Disclosed are bi-specific complexes aimed at inhibiting mast cells, eosinophils and/or basophils, and thus, at inhibiting allergy-type reactions. In particular, said complexes are best exemplified by bi-specific antibodies, which bind to two targets present in the same cell. One target is the inhibitory receptor IRp60. The second target is a cell-specific activator, e.g. IgE, cKIT, FcεRI, IL5R or CCR3. Binding of the bi-specific antibody to its targets results in the induction of an inhibitory pathway, through the inhibition of the signaling from the activator. Compositions and uses of the bi-specific complexes are also described.

9 Claims, 21 Drawing Sheets

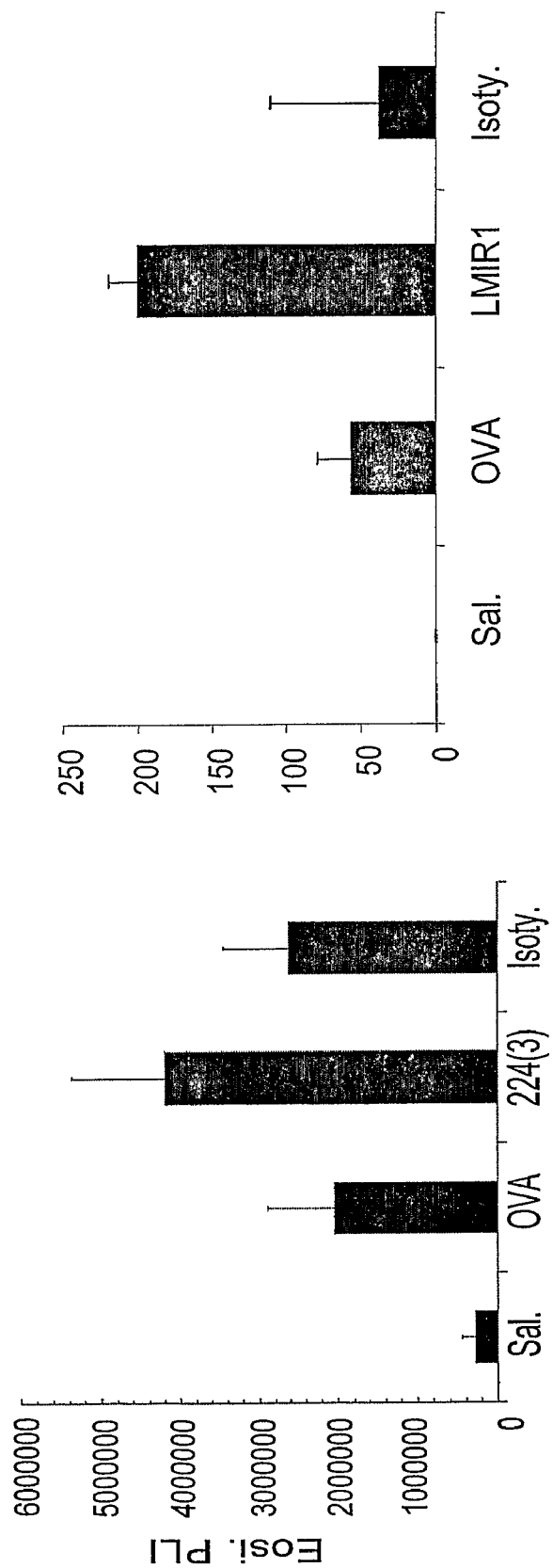

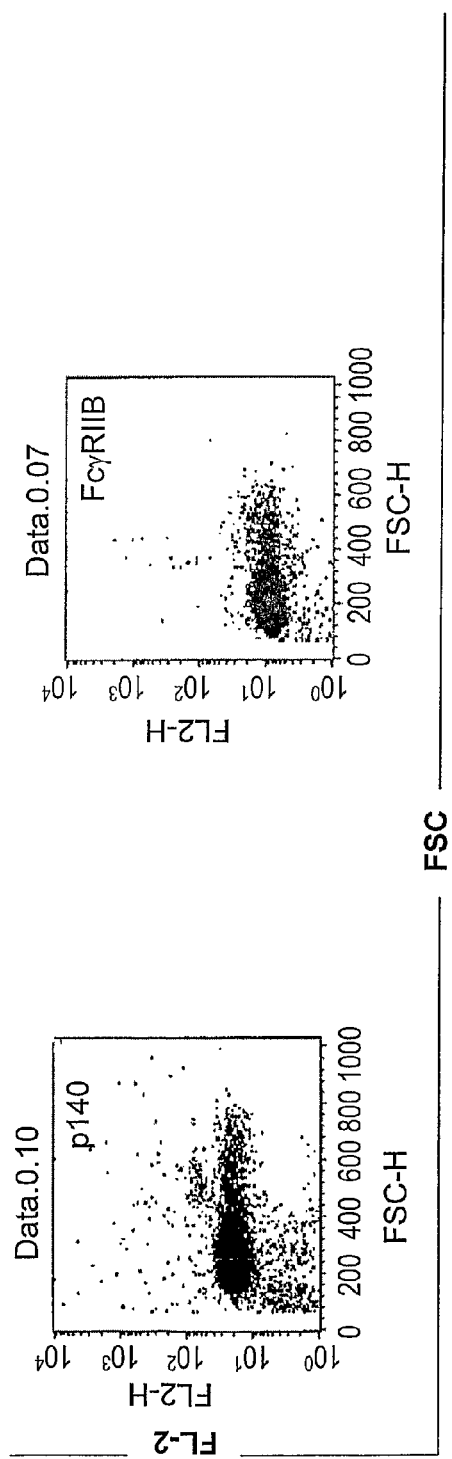
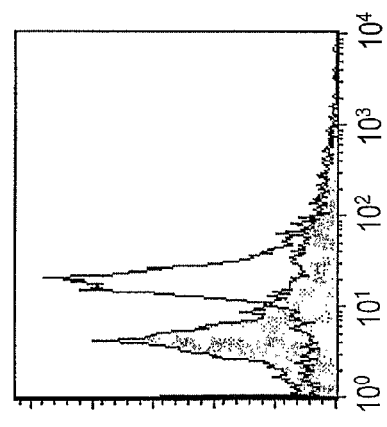
Fig. 9A (cont.)
Fig. 9B

% apopt. ce.

ial Filing Date of Mar. 30, 2005, which claims the
BI-SPECIFIC COMPLEXES FOR TARGETING CELLS INVOLVED IN ALLERGIC-TYPE REACTIONS, COMPOSITIONS AND USES THEREOF

RELATED APPLICATIONS

This application is a National Phase Application of PCT Patent Application No. PCT/IL2005/000358 having an International Filing Date of Mar. 30, 2005, which claims the benefit of U.S. Provisional Patent Application No. 60/557,377 filed on Mar. 30, 2004. The contents of the above Applications are all incorporated herein by reference.

FIELD OF THE INVENTION

The present invention relates to the field of immunopharmacology. More specifically, the present invention refers to a bi-specific molecule which functions as a modulator of allergic inflammation, being both a preventive and therapeutic tool.

BACKGROUND OF THE INVENTION

All publications mentioned throughout this application are fully incorporated herein by reference, including all references cited therein.

A. Allergic Inflammation

Allergic inflammation is a complex phenomenon, involving various cell types such as inflammatory and structural cells. Mast cells are the well-established initiators of allergic inflammation, attracting, activating and finally interacting with other inflammatory cells, mainly the eosinophils. Allergic inflammation comprises a variety of pathologies, such as asthma, allergic rhinitis, allergic conjunctivitis, atopic eczema etc. Among these diseases, and as an example, asthma is the most common illness of early childhood, counting for up to 20% in Western countries and currently increasing [Busse WW, Lemanske RF Jr. (2001) *N Engl J Med.* 344: 3501].

Experimentation in the field of allergy has provided insights into the cellular and molecular mechanisms underlying these pathologies. These investigations have led to the understanding that the allergic response is often biphasic. The first, early phase is initiated by mast cell activation (see below), while the second, late phase is brought about by the infiltration of inflammatory cells, predominantly T-cells, eosinophils and some basophils [Broide D H, Firestein G S. (1991) *J Clin Invest.* 88:10482]. Knowledge, however, has not yet yielded efficacious therapeutic means. Currently used approaches offer either symptomatic relief (i.e. anti-histamines and anti-leukotrienes) or a non-selective anti-inflammatory treatment (i.e. glucocorticosteroids). In addition, newly developed immunopharmacological treatments targeting a single antibody (e.g. IgE), T cell cytokine (e.g. anti-IL-5) or several transcription factors (e.g. STAT-6, GATA-3 or FOG-1) have not proven efficient as yet.

B. Mast Cells

Mast cells are tissue dwelling, FcεRI bearing cells containing prominent cytoplasmic granules. Besides having a pivotal role in allergic reactions, they are also involved in fibrosis, tumors, autoimmune diseases and innate immunity. Mast cells are widely distributed throughout the body, in connective tissues and on mucosal surfaces where they are usually located in close proximity to blood vessels and peripheral nerves. Therefore, they are exposed to environmental stimuli such as microorganisms and allergens with which they can react, both within minutes and/or over a period of hours, and undergo regulated secretion of preformed and newly synthesized mediators.

Upon activation, mast cells release a variety of inflammatory mediators including pre-formed granule constituents (e.g. histamine, proteoglycans and proteases), PGD2, LTC4, PAF, and to a lesser extent, LTB4, and a variety of cytokines (e.g. IL-1, IL-3, IL-4, IL-5, IL-6, IL-8, IL-13, RANTES, IFN-γ, TGF-β, TNF-α, and GM-CSF) [Puxeddu I. et al. (2003) *Int J Biochem Cell Biol.* 35:16013].

In addition to the classical "allergic" IgE-dependent mast cell activation that is triggered by the binding of allergens to two adjacent IgE molecules bound to FcεRI, there are other ways of mast cell stimulation. IgE-independent mast cell activation may be particularly important in the setting of the late phase and in chronic inflammation. Notably, while anti-IgE therapy is now approved for the treatment of asthma, it only induces a modest improvement. This highlights the involvement of non-IgE dependent pathways in the development of asthma as well as the need for new targets for therapeutic intervention. Indeed, work done in the inventors' laboratory (as well as in others) has shown that numerous mediators are capable of activating mast cells [Piliponsky A. M. et al. (2003) *Blood* 101:1898-4; Feldweg, A. M. et al. (2003) *Eur. J. Immunol.* 33:2262-8]. Among them, stem cell factor (SCF), which is critically responsible for mast cell differentiation, survival, proliferation, maturation, chemotaxis, adhesion, as well as activation, and Nerve Growth Factor (NGF) which also induces mast cell activation.

The IgE-independent stimulation of mast cells can also be triggered by polybasic compounds that share similar structural features essential for their activity such as compound 48/80, neuropeptides (VIP, CGRP, substance P, neurotensin), and eosinophil derived-major basic protein (MBP) [Piliponsky A. M. et al. (2003) id ibid.].

Eosinophils are bone marrow-derived granulocytes that differentiate under the regulation of the transcription factors GATA-1&2, and c/EBP, and the cytokines IL-3, GM-CSF and IL-5 ("eosinophil survival cytokines") [Kaatz Maa et al (2004) *Int. J. Mol. Med.* 14:1055-160]. Notably, CD4+Th2 cells are the main producers of these cytokines [Umland SP et al (1998) *Am J Respir Cell Mol Biol* 18:631-42]. Eosinophils normally enter the blood and migrate into the gastrointestinal tract, but in inflammatory states they can accumulate in various tissues. Here they may survive for several days due to effects of the locally released "survival cytokines," before programmed cell death occurs. Eosinophils are associated with host defense mechanisms in parasitic infestations and are implicated in the pathogenesis of allergic, immunological and malignant disorders as well as a variety of idiopathic hypereosinophilic syndromes [Bain, B. J. (2004) *Am J Hematol* 77:82-5; Klion, A. D. et al (2004) *J. Allergy Clin. Immunol.* 113:30-7]. In LAR (late asthmatic response), eosinophils may be responsible for tissue damage (mostly epithelial) through the release of their cytotoxic granule proteins. In addition, evidence is emerging implicating eosinophils as effector cells involved in the tissue repair and fibrosis associated with asthma [Levi-Schaffer, F. et al. (1999) *Proc Natl Acad Sci USA* 96:9660-5].

Eosinophils store preformed granule mediators, like major basic protein (MBP), eosinophil cationic protein (ECP), eosinophil derived neurotoxin (EDN) and eosinophil peroxidase (EPO); synthesize lipid mediators, like PAF, LTC4, and PGE2, as well as proinflammatory and immunoregulatory cytokines and chemokines, like IL-1, IL-2, IL-3, IL-4, IL-6, IL-8, IL-10, IL-13, IL-16, GM-CSF, SCF, NGF, TNF-α, TGF-β, INF-γ, MIP-1, RANTES and eotaxin [Piliponsky, A.

M. et al. (2002) *Mol Immunol* 38:1369]. The eosinophil basic proteins were found to be highly toxic in vitro to respiratory epithelial cells, at concentrations detected in biological fluid from patients with asthma. Furthermore, eosinophils produce matrix metalloproteinase (MMP)-9 and tissue inhibitor of matrix metalloproteinase (TIMP)-1/2. These cells also contain heparanase and are a source for vascular endothelial growth factor (VEGF), platelet derived growth factor (PDGF) and b-fibroblast growth factor (b-FGF) [Munitz, A. et al. (2004) *Allergy* 59:268-75], clearly indicating their role in asthma-associated and fibrosis with asthma.

Activation of eosinophils and consequent mediator release, both in allergic setting and in other diseases can be induced by a series of agonists. In fact, receptors for several pro-inflammatory mediators (i.e. C5a, PAF), cytokines (i.e. IL-5, GM-CSF, IL-3, IL-2, IFNγ etc.), immunoglobulins (i.e. IgG, IgA) and chemokines (i.e. CCR3) [Munitz (2004) id ibid.] are expressed on the eosinophil's surface. However, the role of these receptors in promoting eosinophil activation in vivo (especially in the setting of chronic allergic airway inflammation) is not known. This is not just an academic question, since blockade of eosinophil activation is currently being pursued for the treatment of asthma. Recent results with anti-IL-5 therapy have reaffirmed the need to identify the fundamental mechanisms of eosinophil activation, since this reagent did not have a significant impact on eosinophil degranulation in asthmatics [Kay, A. B. et al (2003) *Am J Respir Crit Care Med* 167:1586-7]. Eosinophils have also been found to express several additional inhibitory/activatory Ig-superfamily cell surface receptors also expressed in mast cells, such as LIR-3/ILT-5, LIR-1/ILT-2, LIR-2/ILT-4, LIR-7/ILT-1 [Tedla N. et al. (2003) *Proc. Natl. Acad. Sci. USA* 100:1174-9] and siglecs [Nutku, E. et al (2003) *Blood* 101:5014-20].

Eosinophils encounter mast cells in the tissue during the late phase of the allergic inflammatory process. Recently, evidence has emerged indicating that there is an important cross-talk between these two cells. Work done in the inventors' laboratory has shown that eosinophil survival is enhanced by mast cell-derived TNF-α via TNF-αRI and TNF-αRII [Temkin, V. et al. (2001) *Cytokine* 15:20-6]. Furthermore, the preformed mast cell-derived tryptase induces IL-6 and IL-8 production and release from human peripheral blood eosinophils by PAR-II initiating the mitogen-activated protein kinase (MAPK)/AP-1 pathway, while GM-CSF produced by IgE-activated mast cells induces eosinophil survival and eosinophil cationic protein (ECP) release. Human lung-derived mast cells become responsive to MBP when co-cultured with fibroblasts, by a process dependent on membrane-bound SCF. Notably, eosinophils also synthesize SCF and NGF. Altogether, all this strengthens the importance of mast cells and eosinophils in the late and chronic stages of allergic inflammation [Temkin V. et al. (2002) *J Immunol.* 169:2662; Hartman M. et al. (2001) *Blood* 97:10865-6; Solomon, A. et al. (1998) *J. Allergy Clin. Immunol.* 102:454-60].

It has recently become clear that mast cell degranulation is regulated by additional surface activatory and inhibitory receptors such as FcγRIIB, gp49A/B1/B2, PIR-B, LIRs/ILTs and sialic acid binding Ig-like lectins (siglecs) that are expressed on mast cells and functional on murine and human mast cells [Katz H R. (2002) *Curr Opin Immunol.* 14:6987].

C. Inhibitory Receptors

It has become increasingly apparent that both mast cells and eosinophils express several inhibitory receptors belonging either to the Ig receptor superfamily (characterized by a single V-type Ig-like domain in the extracellular portion such as KIRs, LIRs/ILTs, LAIR, gp49B1, etc.) or to the c-type (calcium dependent) lectin superfamily (such as MAFA, CD94/NKG2A). This large family of immune inhibitory receptors can be identified by a consensus amino acid sequence, the immunoreceptor tyrosine-based inhibitory motif (ITIM). The ITIM is present in the cytoplasmic domain of these molecules. The archetype ITIM sequence is composed of 6 amino acids (Ile/Val/Leu/Ser)-X-Tyr-X-X-(Leu/Val), where X denotes any amino acid. Upon activation, these inhibitory receptors undergo tyrosine phosphorylation, often by a Src family kinase, which provides a docking site for the recruitment of cytoplasmic phosphatases having a Src homology 2 (SH2) domain such as SHP-1,-2 and SHIP-1,-2 [Ravetch J V, Lanier L L. (2000) *Science*. 290:848].

As previously described, mast cells can be activated by IgE-dependent (FcεRI mediated) or -independent stimuli. Activation of mast cells via IgE-dependent mechanisms results in rapid recruitment of syk and lyn to tyrosine phosphorylated residues in the intracellular component of the FcεRI receptor termed ITAM (immunoreceptor tyrosine-based activatory motif). The consequence of this action is histamine and other preformed mediators release and synthesis, and release of lipid mediators by a rapid process that is completed in less than 30 minutes. In addition, SCF and NGF, which activate mast cells, are dependant on Src family kinases. Interestingly, both IgE-dependent and independent stimuli are regulated by inhibitory receptors at least in vivo in mice models. Thus, recruitment of SHP-1, -2 and SHIP-1,-2 that dephosphorylate ITAM domains or kinase activity result in downregulation of mast cell activation. This inhibition has been thoroughly described for the gp49B1 inhibitory receptor on murine mast cells, where co-ligation of the inhibitory receptor with FcεRI resulted in inhibition of secretory granule mediator (histamine, β-hexosaminidase) and LTC4 release [Katz H. R. et al. (1996) *Proc Natl Acad Sci USA*. 93:10809].

IRp60 (inhibitory receptor protein 60) is an inhibitory receptor belonging to the Ig superfamily. It is expressed on many cell types such as T-cells, NK cells and granulocytes. Cross-linking of IRp60 on NK cells, results in down-regulation of NK cytolyitic activity. In addition, treatment of IRp60 with sodium pervanadate led to marked IRp60 tyrosine phosphorylation and association with both SHP-1 and SHP-2 [Cantoni C. et al. (1999) *Eur J Immunol*. 29:3148]. Furthermore, IRp60 cross-linking inhibited the cytolitic activity of T-cell clones in re-directed killing assays using anti-CD3 mAb. Importantly, the ligand of IRp60 is yet unknown.

D. Bi-Specific Antibodies (BsAb).

In recent years, antibody therapy has become a new treatment modality for a vast array of diseases such as cancer, malaria and asthma. Nonetheless, it is widely agreed that the efficacy of antibodies requires further improvement.

Bi-specific antibodies are proteins that have two different binding specificities, usually designed to recognize two different antigens on different cells. Thus, one binding site is specific for an antigen on the target cell (i.e. infected or cancer cell) while the other binding site recognizes specifically an antigen on the immune effector cell. Accordingly, the effector-cell mechanisms will be exerted upon the target cell leading to an appropriate immune response [Hudson, P. J. et al. (2003) *Nat. Med.* 9:129-34.

First-generation bi-specific antibodies were produced by fusing two established hybridoma cell lines to form quadromas [Milstein C, Cuello A C. (1983) *Nature*. 305:537] or by chemical cross-linking of respective F(ab') fragments [Karpovsky B. et al. (1984) *J Exp Med*. 160:1686]. In vitro, in vivo and clinical studies done with such bi-specific antibodies confirmed the therapeutic potential of such a treatment [van de Winkel J. G. et al. (1997) *Immunol Today.* 18:562].

A novel approach with bi-specific antibodies has been to have the two different antigens to be recognized present in the same cell. Daeron et al. [US 2004/0038894] describe the possibility that a bi-specific antibody which would recognize an inhibitory KIR—Killer cell Immunoglobulin Receptors, which are mostly expressed in NK cells and function as cell surface receptors for MHC Class I molecules—and simultaneously a stimulatory receptor, e.g. ITAM-bearing receptors such as an activating Ig receptor, FcεRI, CD3/TCR, to cite just a few, would have the ability to cross-link said stimulatory receptor with said KIR, intra- or extra-cellularly. Said cross-linking would then result in the regulation of the activation of said stimulatory receptor, to which the ultimate outcome would be the modulation of immune and inflammatory responses. This prediction is actually confirmed by Tam et al. [Tam, S. W. et al. (2004) Allergy 59(7):772], who described the generation of a bi-specific antibody against human IgE and human FcεRII. Said antibody was able to inhibit antigen-induced histamine release by human mast cells and basophils.

The present inventors have characterized the expression of inhibitory receptors in mast cells and eosinophils, and particularly the expression of the inhibitory receptor IRp60 in these cells (see Examples below).

In the present invention, the inventors describe the generation of bi-specific antibodies that are able to bind and activate the inhibitory receptor IRp60 in a cell-specific manner, due to its target-cell specific module.

The particular focus of the present study is to target cells involved in the allergic response, like mast cells, eosinophils and basophils, and therefore provide a new, more efficient, cell specific agent for the treatment of allergy-related illnesses.

Thus, it is an object of the present invention to provide a BsAb which recognizes and activates the inhibitory receptor IRp60 (first component of the BsAb) and one other marker (second component of the BsAb) specific for mast cells, eosinophils or basophils, said marker being an activator (or a receptor) whose signal transduction pathway is inhibited by the activation of the inhibitory receptor (i.e., the first component of the BsAb).

Other uses and objects of the invention will become clear as the description proceeds.

SUMMARY OF THE INVENTION

In a first aspect, the present invention relates to a bi-specific complex for targeting a target cell, wherein said complex comprises two different target recognition components, each of said components comprising a molecule which specifically binds to a first and second targets located on said target cell, respectively, or any functional fragment thereof, wherein one target is the inhibitory receptor IRp60 or homologues thereof, and the second target is a cell specific activator which activates the inhibitory pathway mediated by said inhibitory receptor. Most importantly, the binding of said complex to said target cell inhibits allergic-type reactions.

In one embodiment, said target recognition components are linked via any one of a cross-linker, a linker compound, a carrier, a synthetic spacer, an immobilizing substrate and a $(Gly_4Ser)_3$ motif based flexible region. Preferably, said target recognition components are cross-linked.

In another embodiment, said cell is derived from the hematopoietic lineage, and is preferably one of a mast cell, an eosinophil and a basophil.

In a further embodiment, the second target of said bi-specific complex may be selected from the group consisting of: immunoglobulins, Fc receptors, cytokine receptors, growth factor receptors, adhesion molecules, Ig-superfamily receptors, chemokine receptors, inflammatory mediator receptor, hormone receptors, complement factor receptors, protease-activated receptors and enzymes.

The recognition component of the bi-specific complex may be selected from any one of a naturally occurring, synthetic or recombinant antibody, single chain Fv (scFv), bi-funcitonal scFv, diabody, F(ab) unit, F(ab') unit, bi-specific F(ab') conjugate, chemically cross-linked bi-functional antibody, linear antibody, F(ab')$_2$ antigen binding fragment of an antibody, or any functional fragments thereof. Preferably the recognition component is a bi-specific F(ab') conjugate, i.e., two F(ab') units linked together.

In one particular embodiment, said target cell of the bi-specific complex is a mast cell, and said second target is one of IgE, cKIT and FcεRI.

In one specific embodiment, the invention provides a bi-specific complex for targeting a target cell, wherein said complex comprises a bi-specific F(ab') conjugate, recognizing IRp60, or any homologues thereof, and IgE.

In this specific embodiment, the F(ab') units correspond to F(ab') fragments of two different antibodies, one against IRp60 and one against IgE.

In another specific embodiment, the invention provides a bi-specific complex for targeting a target cell, wherein said complex comprises a bi-specific F(ab') conjugate, recognizing IRp60 or any homologues thereof, and cKIT.

In a further specific embodiment, the invention provides a bi-specific complex for targeting a target cell, wherein said complex comprises a bi-specific F(ab') conjugate, recognizing IRp60 or any homologues thereof, and FcεRI.

Any one of the above-mentioned bi-specific complexes may function as an inhibitor of mast cell activity.

In another particular embodiment, said target cell is an eosinophil, and said second target is one of IL-5 receptor (IL-5R) and the receptor to eotaxin (CCR3). Thus, the bi-specific complex of the invention may be a complex comprising a bi-specific F(ab') conjugate, recognizing IRp60 or any homologues thereof, and IL-5R or CCR3. Said complex may function as an inhibitor of eosinophil activity.

The bi-specific complexes described in the present invention may function as inhibitors of allergy effector cell activity, and are especially suitable for treating conditions induced by one of allergic reactions and mast cell- and/or eosinophil-and/or basophil-mediated reactions. Said conditions are selected from the group consisting of: allergic asthma, allergic rhinitis, seasonal allergic conjunctivitis, atopic dermatitis and atopic eczema, allergic disorders and responses to various allergens, systemic anaphylaxis, systemic mastocytosis, morphea/urticaria pigmentosa, mast cell leukemia, atherosclerosis, graft rejection, multiple sclerosis, fibrotic lung diseases, neurofibromatosis, keloids, scleroderma, rheumatoid arthritis, osteoarthritis, acute gout, ocular cicatricial pemphigoid, Crohn's disease, peritoneal adhesions, chronic graft versus host disease (cGVHD), eosinophil myalgia syndrome, extrinsic bronchial asthma, nasal polyposis, Wegener's granulomatosis, intrinsic bronchial asthma, interstitial and other pulmonary diseases, chronic eosinophilic pneumonia, hypersensitivity pneumonitis, allergic bronchopulmonary aspergillosis, sarcoidosis, idiopathic pulmonary fibrosis, neoplastic and myeloproliferative diseases, T cell lymphomas and Hodgkin's disease.

Bi-specific complexes where the second recognition target is IgE, cKIT or FcεRI are especially suitable for use as agents in the treatment of mast cell associated conditions, wherein said conditions are particularly allergic asthma, allergic rhinitis, seasonal allergic conjunctivitis, atopic dermatitis and atopic eczema, allergic disorders and responses to various allergens, systemic anaphylaxis, systemic mastocytosis, morphea/urticaria pigmentosa, mast cell leukemia, atherosclerosis, graft rejection, multiple sclerosis, fibrotic lung diseases, neurofibromatosis, keloids, scleroderma, rheumatoid arthritis, osteoarthritis, acute gout, ocular cicatricial pemphigoid, Crohn's disease, peritoneal adhesions, chronic graft versus host disease (GVHD).

Bi-specific complexes where the second recognition target is IL-5R or CCR3 are especially suitable for use as agents in the treatment of eosinophil-associated conditions, wherein said conditions are particularly extrinsic bronchial asthma, allergic rhinitis, onchocercal dermatitis, atopic dermatitis, nasal polyposis, nodules, eosinophilia, rheumatism, dermatitis, and swelling (NERDS), vasculitic granulomatous diseases, temporal vasculitis, Churg-Strauss syndrome, polyarteritis, Wegener's granulomatosis, multiple sclerosis, graft rejection, intrinsic bronchial asthma, interstitial and other pulmonary diseases, eosinophilic pleural effusions, transient pulmonary eosinophilic infiltrates (Löffler), histiocytosis, chronic eosinophilic pneumonia, hypersensitivity pneumonitis, allergic bronchopulmonary aspergillosis, sarcoidosis, idiopathic pulmonary fibrosis, topical eosinophilia, cat scratch disease, afebrile tuberculosis, chlamydial pneumonia at infancy, neoplastic and myeloproliferative diseases, bronchogenic carcinoma, hypereosinophilic syndrome, T cell lymphomas and Hodgkin's disease, Crohn's disease, vernal keratoconjunctivitis, juvenile inflamed conjunctivitis nevus, Kimura's disease, Gleich's disease.

In another aspect, the present invention provides a pharmaceutical composition comprising as active agent a bi-specific complex as described herein. Said pharmaceutical composition may be for medical use.

In one embodiment, said pharmaceutical composition comprises as active agent a bi-specific complex where the second recognition target is one of IgE, cKIT and FcεRI and is especially suitable for use in the treatment of any disease or condition derived from mast cell hyperactivity or hyperplasia. Said diseases are selected from the group consisting of: allergic asthma, allergic rhinitis, allergic conjunctivitis, atopic dermatitis and atopic eczema, allergic disorders and responses to various allergens, systemic anaphylaxis, systemic mastocytosis, morphea/urticaria pigmentosa, mast cell leukemia, atherosclerosis, graft rejection, multiple sclerosis, fibrotic lung diseases, neurofibromatosis, keloids, scleroderma, rheumatoid arthritis, osteoarthritis, acute gout, ocular cicatricial pemphigoid, Crohn's disease, peritoneal adhesions, chronic GVHD, bronchial asthma, nasal polyposis, Wegener's granulomatosis, interstitial and other pulmonary diseases, chronic eosinophilic pneumonia, hypersensitivity pneumonitis, allergic bronchopulmonary aspergillosis, sarcoidosis, idiopathic pulmonary fibrosis, neoplastic and myeloproliferative diseases, T cell lymphomas and Hodgkin's disease.

In another embodiment said pharmaceutical composition comprises as active agent a bi-specific complex where the second recognition target is IL-5R or CCR3, and is especially suitable for use in the treatment of any disease or condition derived from eosinophil hyperactivity or hyperplasia. Said conditions are selected from the group consisting of extrinsic bronchial asthma, allergic rhinitis, onchocercal dermatitis, atopic dermatitis, nasal polyposis, nodules, eosinophilia, rheumatism, dermatitis, and swelling (NERDS), vasculitic granulomatous diseases, temporal vasculitis, Churg-Strauss syndrome, polyarteritis, Wegener's granulomatosis, multiple sclerosis, graft rejection, bronchial asthma, interstitial and other pulmonary diseases, eosinophilic pleural effusions, transient pulmonary eosinophilic infiltrates (Löffler), histiocytosis, chronic eosinophilic pneumonia, hypersensitivity pneumonitis, allergic bronchopulmonary aspergillosis, sarcoidosis, idiopathic pulmonary fibrosis, topical eosinophilia, cat scratch disease, afebrile tuberculosis, chlamydial pneumonia at infancy, neoplastic and myeloproliferative diseases, bronchogenic carcinoma, hypereosinophilic syndrome, T cell lymphomas and Hodgkin's disease, Crohn's disease, vernal keratoconjunctivitis nevus, Kimura's disease, Gleich's disease.

The pharmaceutical composition of the invention may further comprise buffers, additives, stabilizers, diluents and/or excipients, and may also be designated a pharmaceutical formulation.

In a further aspect, the present invention regards the use of the bi-specific complex described in the invention in the preparation of a pharmaceutical composition for the treatment of any disease or condition associated with mast cell and/or eosinophil hyperactivity or hyperplasia, wherein said disease is selected from the group consisting of: allergic asthma, allergic rhinitis, allergic conjunctivitis, atopic dermatitis and atopic eczema, allergic disorders and responses to various allergens, systemic anaphylaxis, systemic mastocytosis, morphea/urticaria pigmentosa, mast cell leukemia, atherosclerosis, graft rejection, multiple sclerosis, fibrotic lung diseases, neurofibromatosis, keloids, scleroderma, rheumatoid arthritis, osteoarthritis, acute gout, ocular cicatricial pemphigoid, Crohn's disease, peritoneal adhesions, chronic graft versus host disease (GVHD), eosinophil myalgia syndrome, bronchial asthma, nasal polyposis, Wegener's granulomatosis, interstitial and other pulmonary diseases, chronic eosinophilic pneumonia, hypersensitivity pneumonitis, allergic bronchopulmonary aspergillosis, sarcoidosis, idiopathic pulmonary fibrosis, neoplastic and myeloproliferative diseases, T cell lymphomas and Hodgkin's disease.

One particular embodiment of this aspect of the invention is the use of the bi-specific complex wherein the second recognition target is IgE, cKIT or FcεRI, or a pharmaceutical composition comprising thereof, in the inhibition of mast cell function.

Another particular embodiment of this aspect of the present invention is the use of the bi-specific complex wherein the second recognition target is IL-5R or CCR3, or a pharmaceutical composition comprising thereof, in the inhibition of eosinophil function.

In an even further aspect the present invention provides a method of treatment of any disease or condition associated with mast cell hyperactivity and hyperplasia, comprising administering a therapeutically effective amount of the bi-specific complex of the invention wherein the second recognition target is IgE, cKIT or FcεRI, or a composition comprising thereof, to a subject in need.

In another further aspect the present invention provides a method of treatment of any disease or condition derived from eosinophil hyperactivity and hyperplasia, comprising administering a therapeutically effective amount of the bi-specific complex of the invention wherein the second recognition target is IL-5R or CCR3, or a composition comprising thereof, to a subject in need.

In addition the present invention also provides a method of inhibiting mast cell activity comprising contacting mast cells with the bi-specific complex of the bi-specific complex of the invention wherein the second recognition target is IgE, cKIT or FcεRI, or a composition comprising thereof, for a suitable amount of time.

Alternatively a method of inhibiting eosinophil activity is provided, comprising contacting eosinophils with the bi-specific complex of the invention wherein the second recognition target is IL-5R or CCR3, or with a composition comprising thereof, for a suitable amount of time.

The invention will be described in more detail on hand of the following Figures.

BRIEF DESCRIPTION OF THE FIGURES

FIG. 2A: Human mast cells express IRp60. FACS analysis of IRp60 expression on CBMC and HLMC. IRp60 was detected on CBMC [left] and HLMC [right] using a monoclonal anti-IRp60 antibody followed by anti-mouse-FITC. Black peaks represent negative isotype controls. White peaks represent anti-IRp60 staining. Representative of n=10 [CBMC] and n=3 [HLMC].

FIG. 2B: IRp60 expression is modulated by eosinophil major basic protein (MBP). CBMC were incubated with eosinophil derived MBP [left] or poly-L-Arginine [right] for 24 hours, and IRp60 expression was analyzed by FACS. Blackened peaks [iso] represent negative isotype controls using IgG. Grey peaks [EM] represent anti-IRp60 staining of CBMC treated with enriched medium alone. White peaks represent anti-IRp60 staining of either MBP-treated [left] or poly-L-Arginine-treated [right] CBMC.

FIG. 3B: Percent release of IL-4 from IgE-activated CBMC following stimulation with anti-IRp60.

CBMC were incubated in anti-IRp60 coated plate and activated with anti-IgE antibody for 30 min. The release levels of β-hexosaminidase and tryptase were evaluated by enzymatic-chromogenic assays as described, and expressed as % release. IL-4 release level was evaluated by ELISA, and expressed in pg/mL. Release of β-hexosaminidase was evaluated as described. EM, enriched medium alone; X, cross-linkers [sheep anti-mouse, goat anti-mouse IgE]; anti-IRp60, anti-IRp60-coated well; IgG, isotype-coated well.

Figure 4:
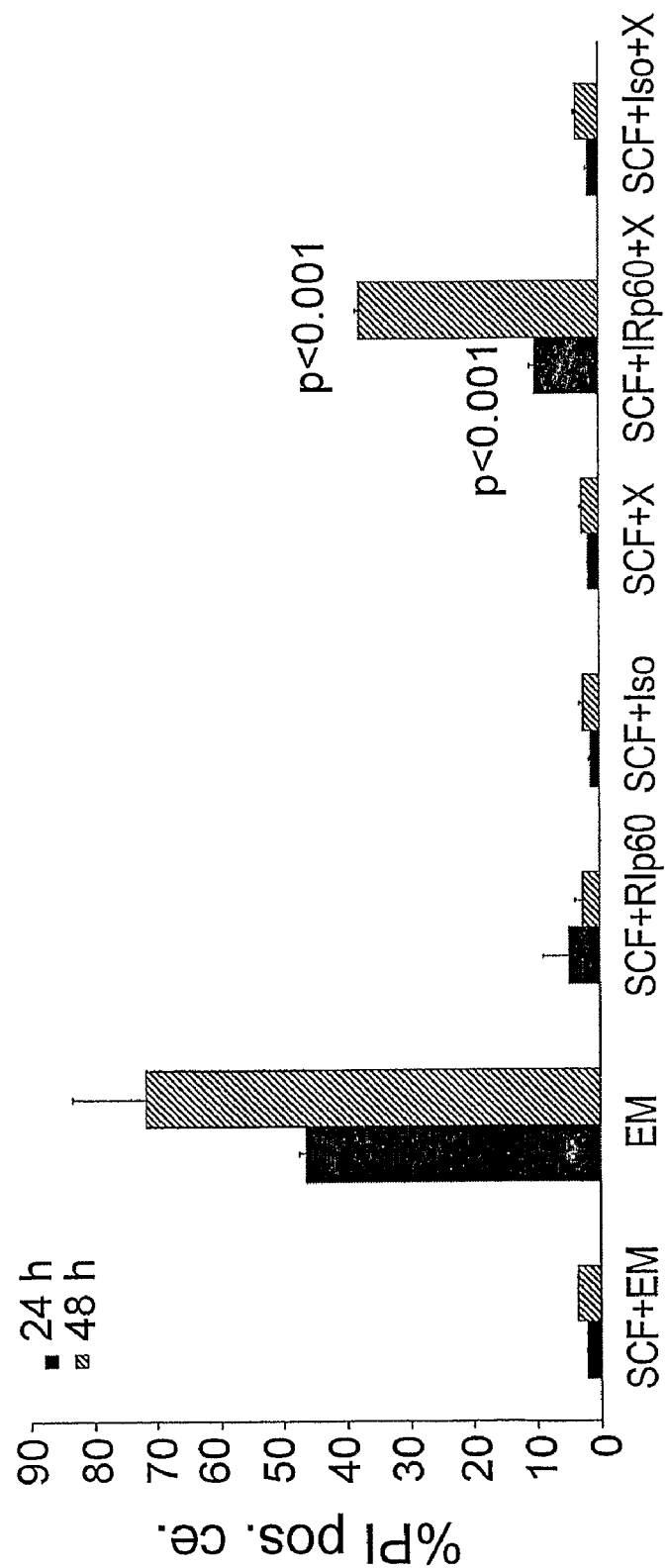

FIG. 4: IRp60 cross-linking inhibits SCF-induced CBMC survival. CBMC were incubated with or without SCF [100 ng/mL] in a anti-IRp60 coated plate for 24 and 48 hours, stained for propidium iodide [PI], and cells positive for PI were analyzed by FACS. Data are presented as % of PI-positive cells of the total. EM, enriched medium alone; X, cross-linkers [sheep anti-mouse, goat anti-mouse IgE]; IRp60, anti-IRp60-coated well; Iso, isotype-coated well.

Figure 5:
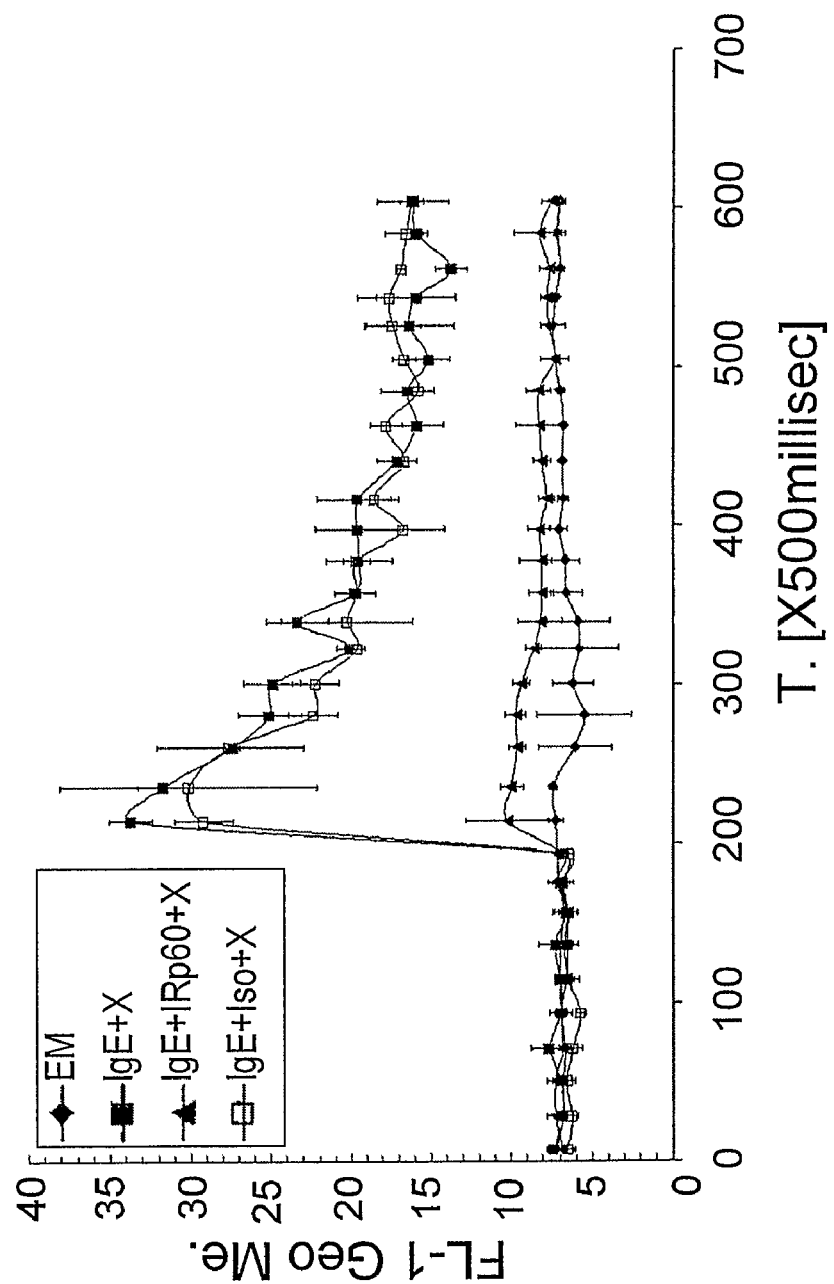

FIG. 5: IRp60 cross-linking inhibits IgE-induced [Ca$_{2+}$] influx. IRp60 on CBMC was cross-linked by incubation with anti-IRp60 and sheep-anti mouse antibodies, and the cells were loaded with Calcium Green-1AM. [Ca$_{2+}$] is represented by FL-1 geo mean. EM enriched medium alone; X cross-linkers [sheep anti-mouse, goat anti-mouse IgE]; IRp60, anti-IRp60; Iso, isotype.

Figure 6A:
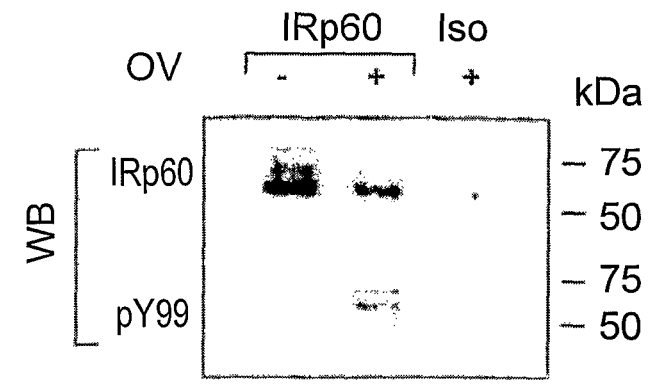
Figure 6A:
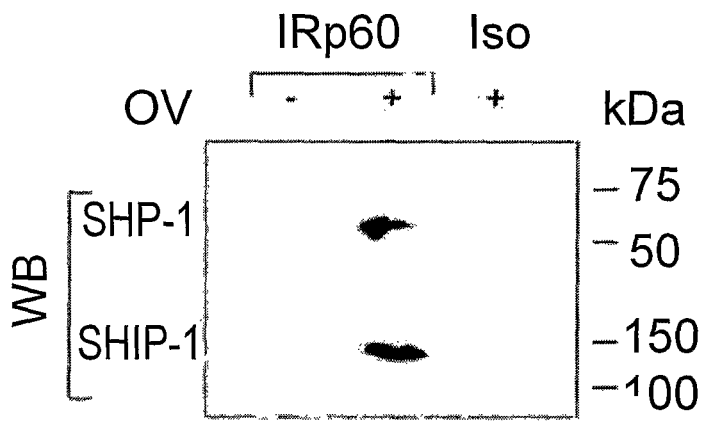
Figure 6B:
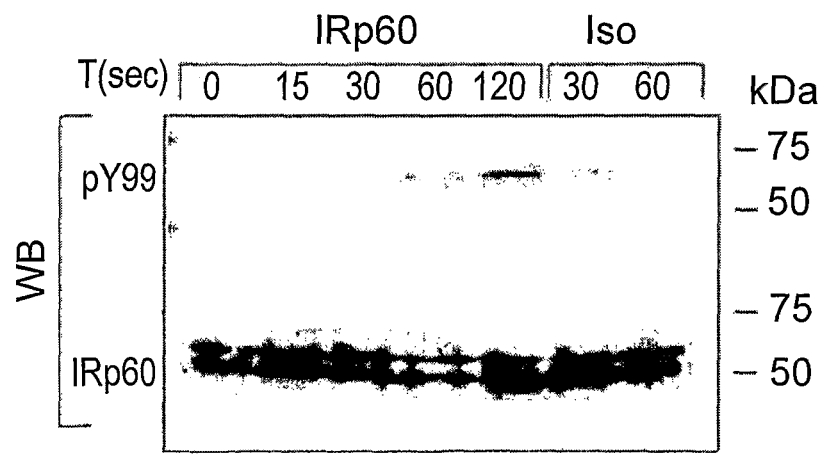

FIGS. 6A-6B: IRp60 tyrosine phosphorylation and phosphatase recruitment.

FIG. 6A: CBMC were treated with sodium orthovanadate. IRp60 was precipitated using anti-IRp60 or IgG1 [negative control] and blotted vs. phosphotyrosine [pY99], SHP-1,2 and SHIP-1.

FIG. 6B: IRp60 tyrosine phosphorylation is dependent on receptor cross-linking. CBMC were incubated in anti-IRp60/IgG1-coated wells for 0, 15, 30, 60 and 120 sec, or in IgG-coated plate for 30 and 60 sec, followed by precipitation and western blot vs. phosphotyrosine [pY99] or IRp60 as a control for protein quantity.

Figure 7:
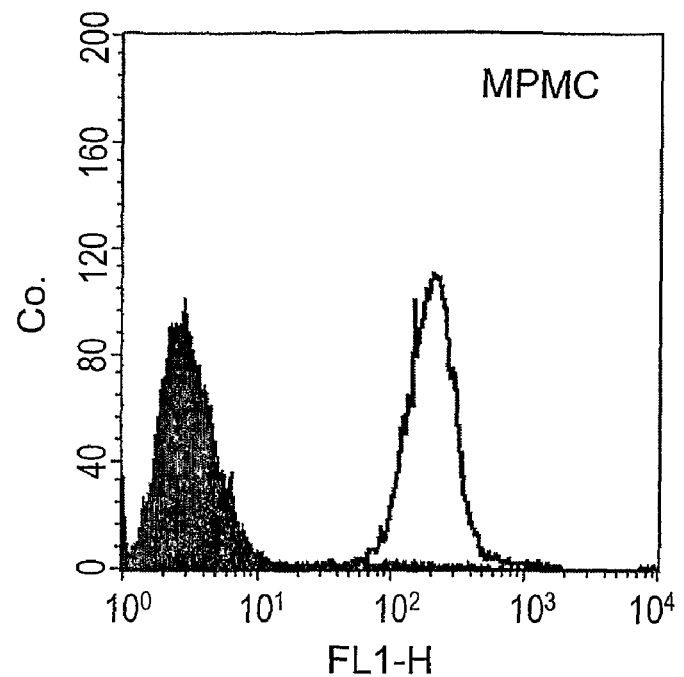
Figure 7:
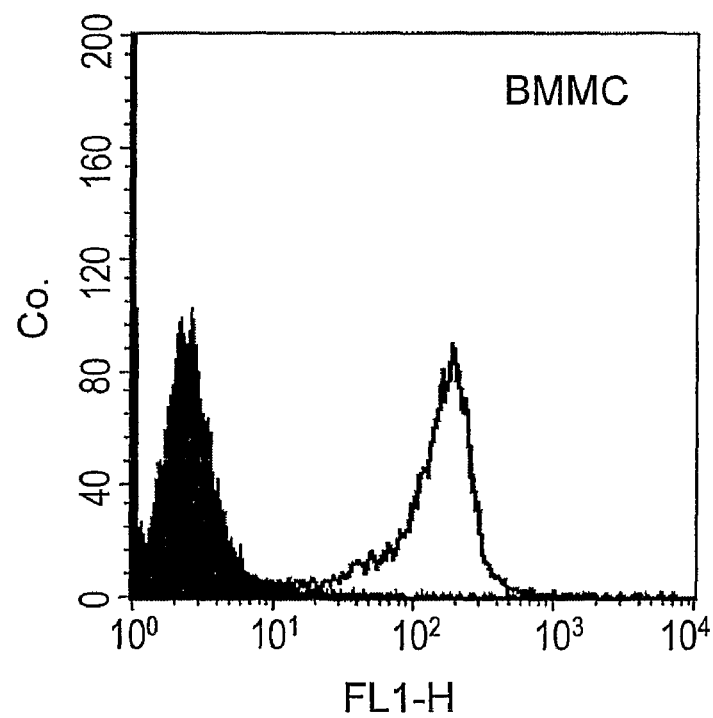

FIG. 7: Mouse mast cells express LMIR1.

Bone marrow mast cells and freshly isolated peritoneal mast cells from BALB/c mice were stained a monoclonal antibody and analyzed by FACS. BMMC, bone marrow mast cells; MPMC, peritoneal mast cells.

FIGS. 8A-8D: LMIR1 neutralization leads to an augmented mast cell activation and consequent eosinophil infiltration in a mouse model of allergic peritonitis.

OVA-induced allergic peritonitis was induced as described, sacrificed at 45 min or 48 hr after OVA-challenge and peritoneal cavity was lavaged for mediator analysis and cell counts, and flow cytometry, respectively. Tryptase and β-hexosaminidase levels were evaluated using enzymatic-chromogenic assays as described. Cells from lavage collected 48 hr following the challenge were stained for CCR3 and analyzed by FACS.

Figure 8A:
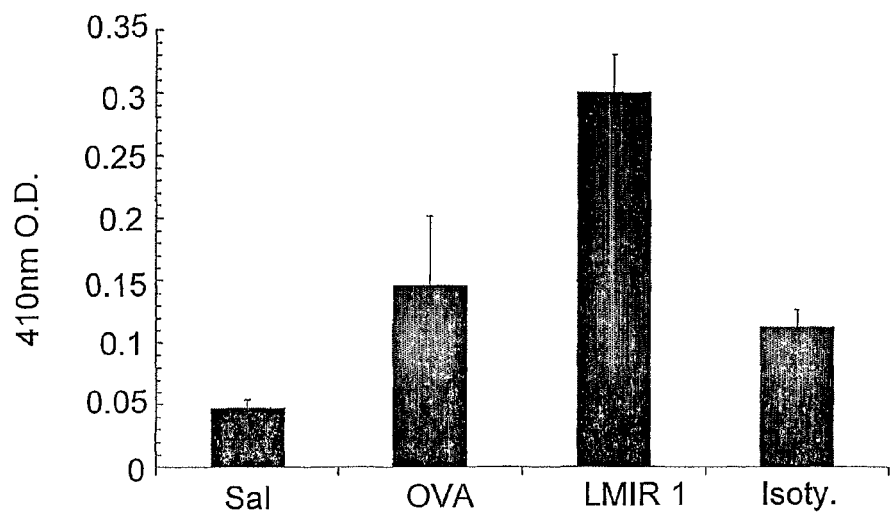

FIG. 8A: LMIR1 neutralization led to a dramatic increase in peritoneal tryptase levels 45 mins after challenge.

Figure 8B:
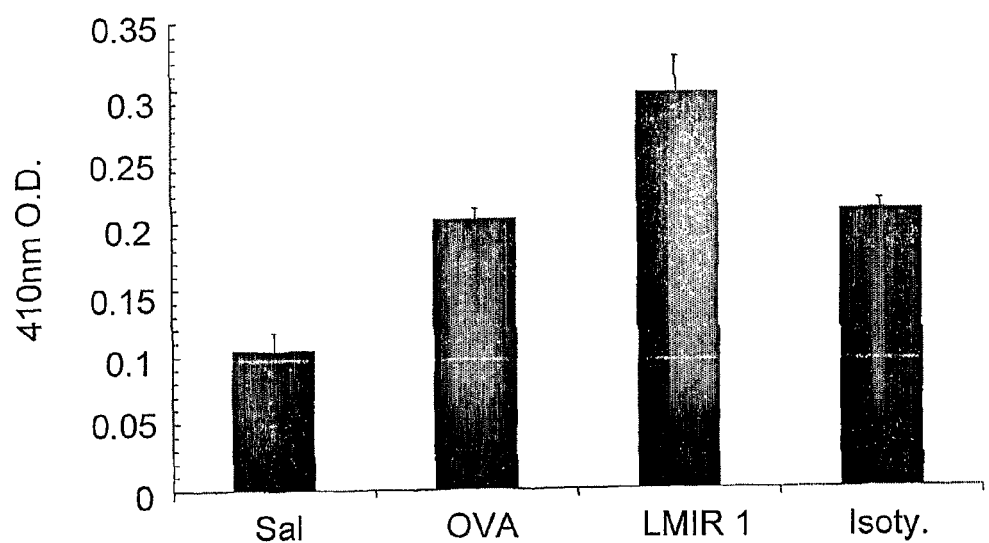

FIG. 8B: LMIR1 neutralization led to a dramatic increase in peritoneal β-hexosaminidase levels 45 mins after challenge.

FIG. 8C: An increased number of eosinophils infiltrated the peritoneal cavity following LMIR1 neutralization (24 hrs after challenge).

FIG. 8D: LMIR1 neutralization led to a dramatic increase in peritoneal eotaxin-2 levels 24 hrs after challenge.

Figure 9A:
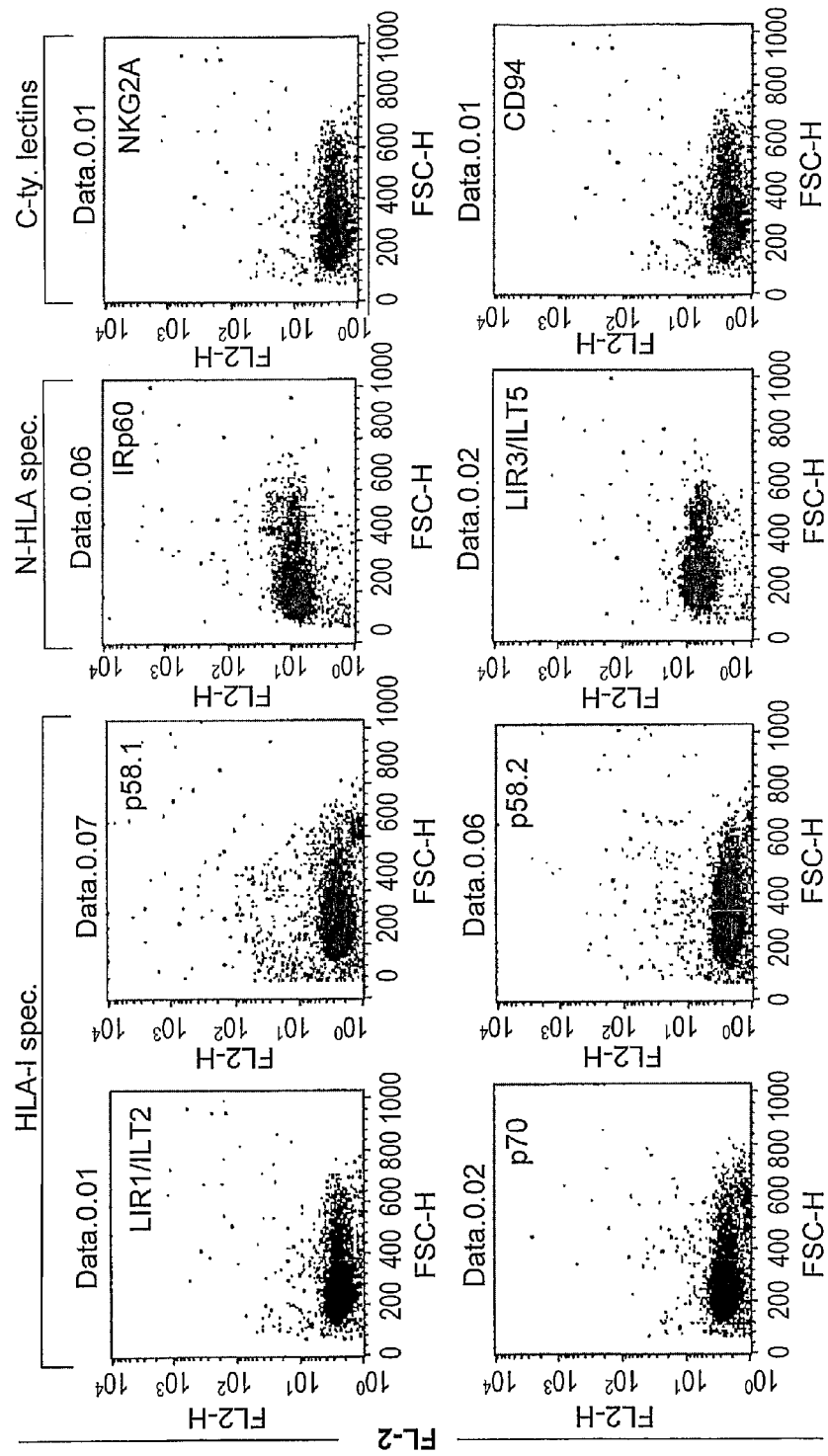

FIGS. 9A-9B: IRp60 is expressed in human eosinophils.

FIG. 9A: Expression pattern of inhibitory receptors on human mast cells. FACS analysis showing the expression levels of IRp60, p140, LIR3/ILT5, FcγRIIB, LIR1/ILT2, LIR3/ILT5, p58.1, p58.2, p70, and NKG2A/CD94 (n=10) in CBMC.

FIG. 9B: Nasal polyp eosinophils express significant levels of IRp60. Left peak corresponds to the isotype control matched antibody, while the right peak shows the staining for IRp60.

Figure 10A:
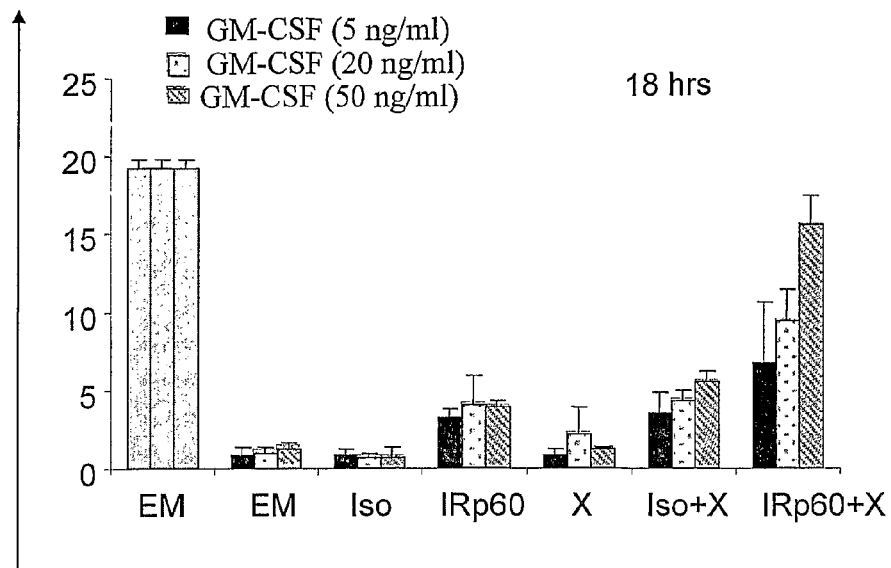
Figure 10B:
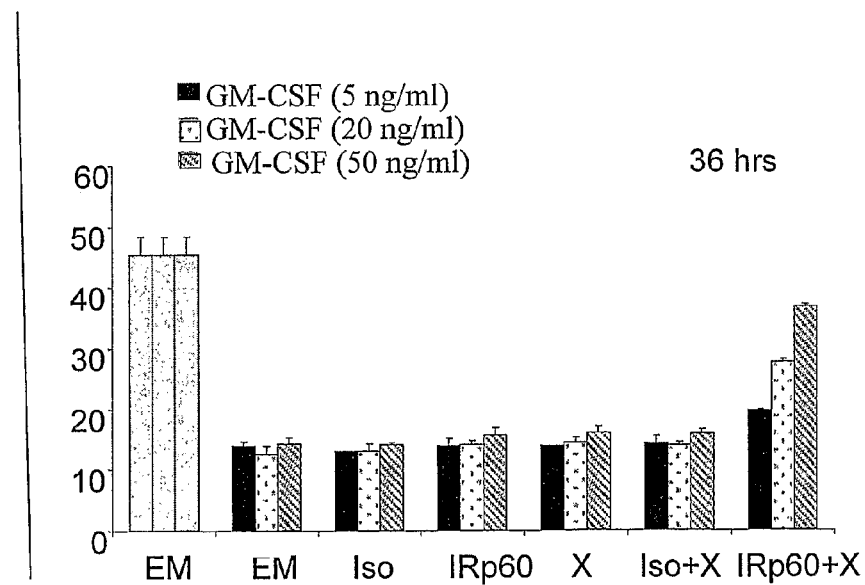

FIGS. 10A-B: IRp60 inhibits gM-CSF mediated survival of human eosinophils.

Graphs show the percent of apoptotic eosinophils after cross-linking with anti-IRp60 or isotype matched control and sheep-anti mouse, and treatment with the indicated concentrations of GM-CSF at various time points.

FIG. 10A: After 18 hrs incubation with GM-CSF.

FIG. 10B: After 36 hrs incubation with GM-CSF.

Figure 11A:
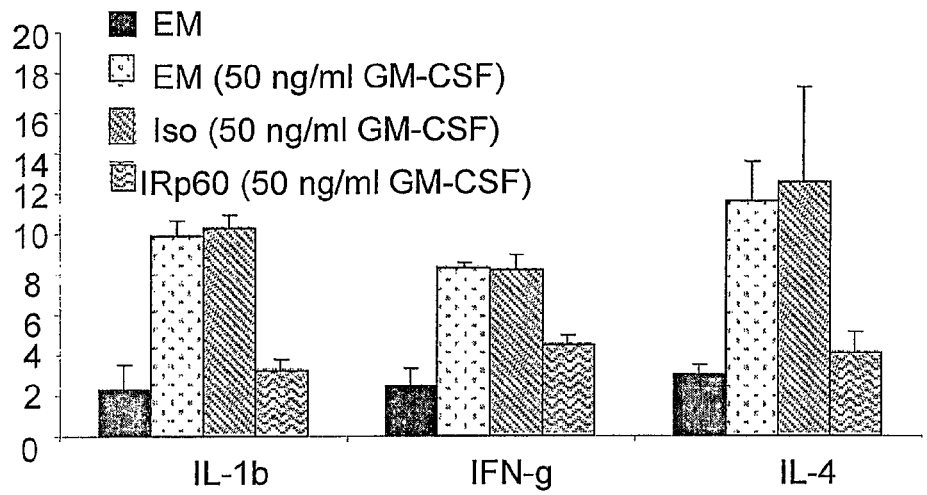
Figure 11B:
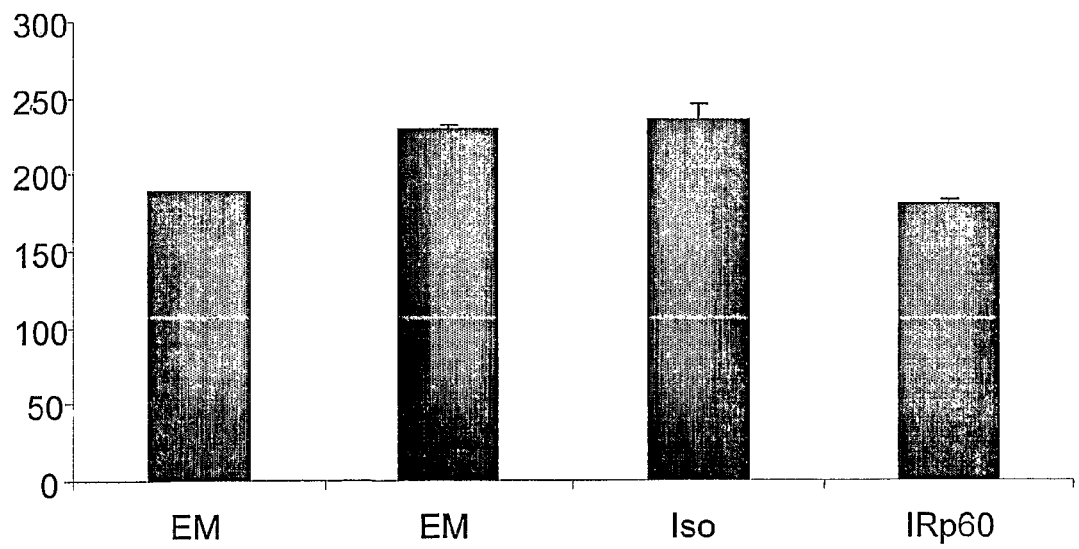

FIGS. 11A-B: IRp60 inhibits GM-CSF mediated activation of human eosinophils.

FIG. 11A: Histogram showing GM-CSF mediated release of IL-1β, IL-4 and IFN-γ, which was significantly inhibited upon cross-linking of IRp60.

FIG. 11B: Histogram showing GM-CSF mediated release of IL-8, which was completely blocked upon cross-linking of IRp60.

Figure 12A:
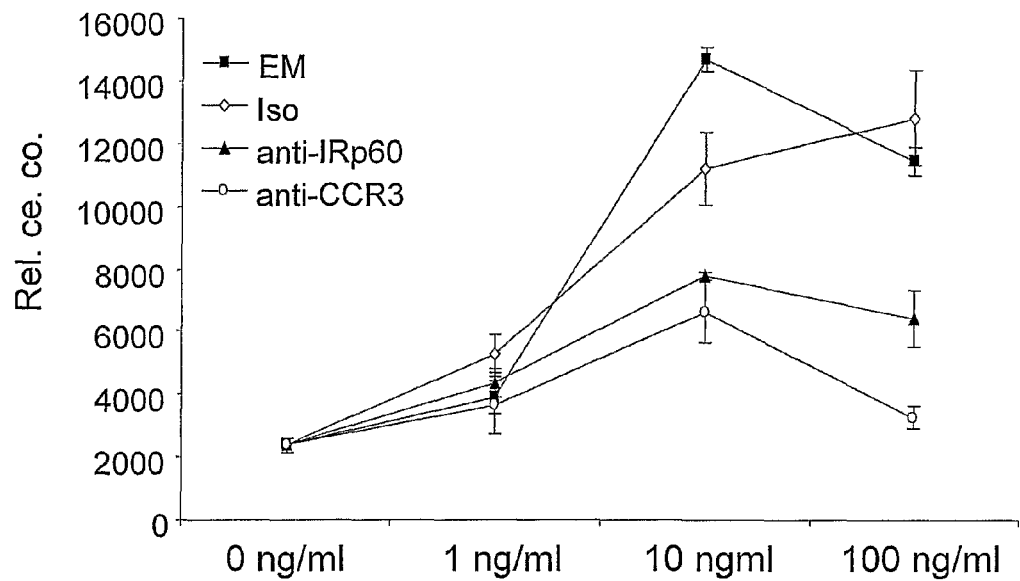
Figure 12B:
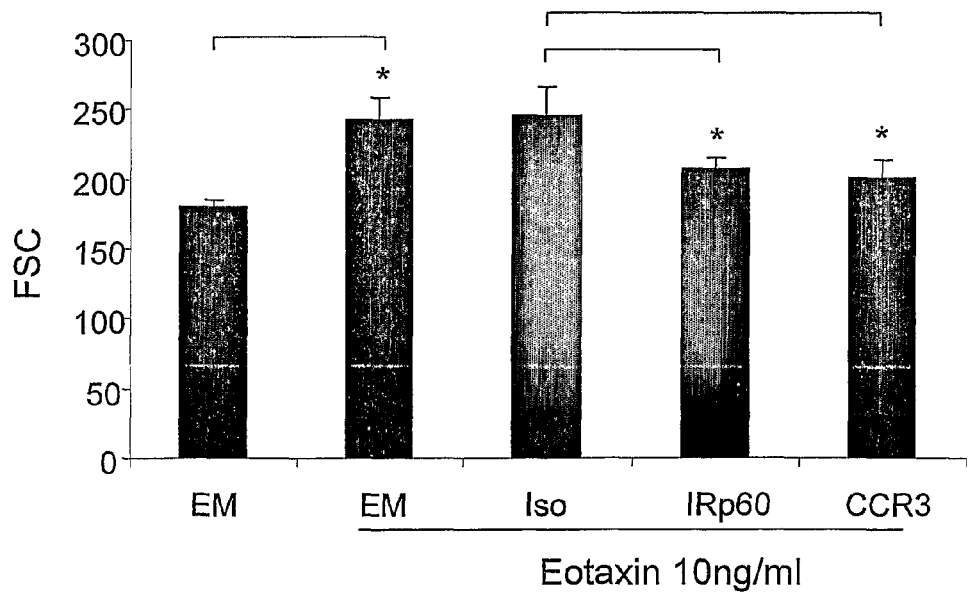

FIGS. 12A-12B: IRp60 inhibits eotaxin-dependent chemotaxis of human eosinophils.

FIG. 12A: Graph shows the number of eosinophils after treatment with anti-IRp60, anti-CCR3, isotype (Iso) or rich medium alone (EM) that moved towards the different concentrations of eotaxin.

FIG. 12B: Histogram shows eotaxin-induced shape change in eosinophils, following incubation with anti-IRp60, anti-CCR3, isotype (Iso) or rich medium alone (EM), and measured by FACS.

Figure 13A:
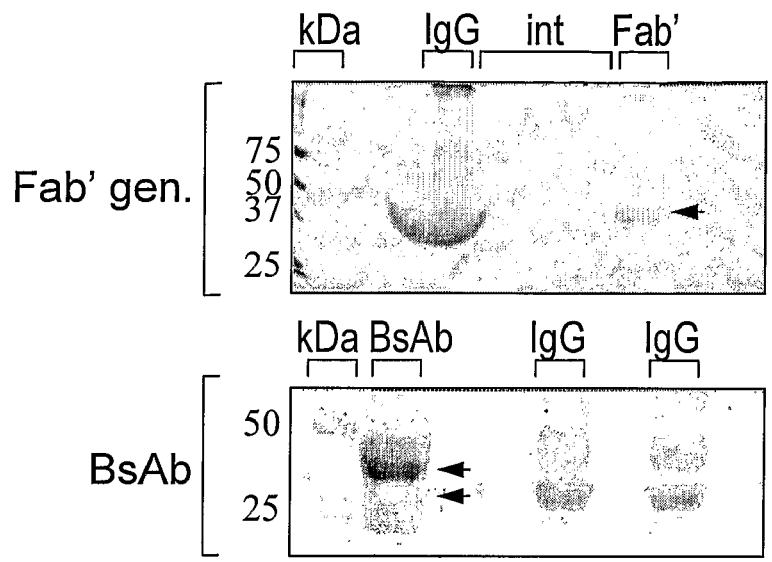
Figure 13B:
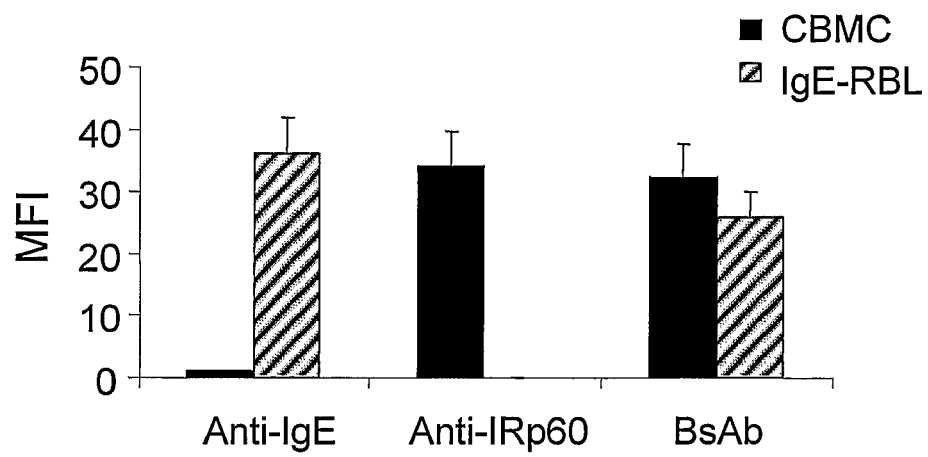

FIGS. 13A-13B: Generation and characterization of a bispecific F(ab')2 fragment.

FIG. 13A: In order to monitor possible material loss, samples from each step in the synthesis of the bi-specific F(ab') were run on native SDS-PAGE [Fab' generation: kDa, size marker; IgG, starting antibody; int, samples from 3 gel filtration stages; Fab', resulting Fab' fragment ready for coupling]. After coupling, reducing SDS-PAGE was run to confirm the BsAb complexion [BsAb: kDa, size marker; BsAb, bispecific antibody; IgG, whole antibody controls]. The BsAb heavy chain is clearly trimmed at ~37 kDa.

FIG. 13B: BsAb bispecificity evaluation by FACS. Anti-human IgE, anti-human IRp60 or IE1 were used to stain both fresh, non-sensitized human mast cells [CBMC] and RBL cells sensitized with human IgE [IgE-RBL] followed by anti-mouse FITC. Staining was expressed as the mean fluorescent intensity [MFI] at the FL-1 channel.

Figure 14:
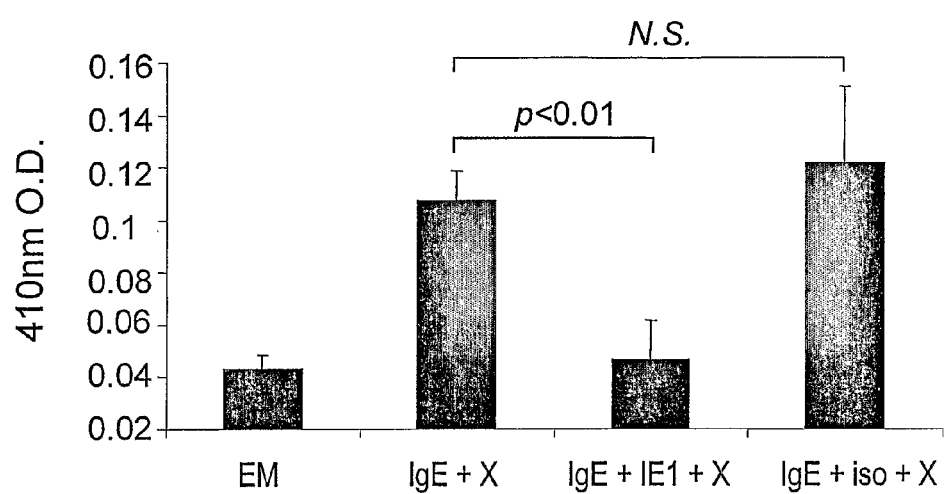

FIG. 14: IE1 inhibits IgE-induced mast cell degranulation in vitro.

IgE-sensitized human mast cells were incubated with 5 μg/mL of IE1 or isotype control for 30 min prior to anti-IgE mediated activation. The release of β-hexosaminidase was measured using a chromoenzymatic assay [EM, enriched medium-treated cells; X, anti-IgE treatment; iso, matching isotype control].

Figure 15A:
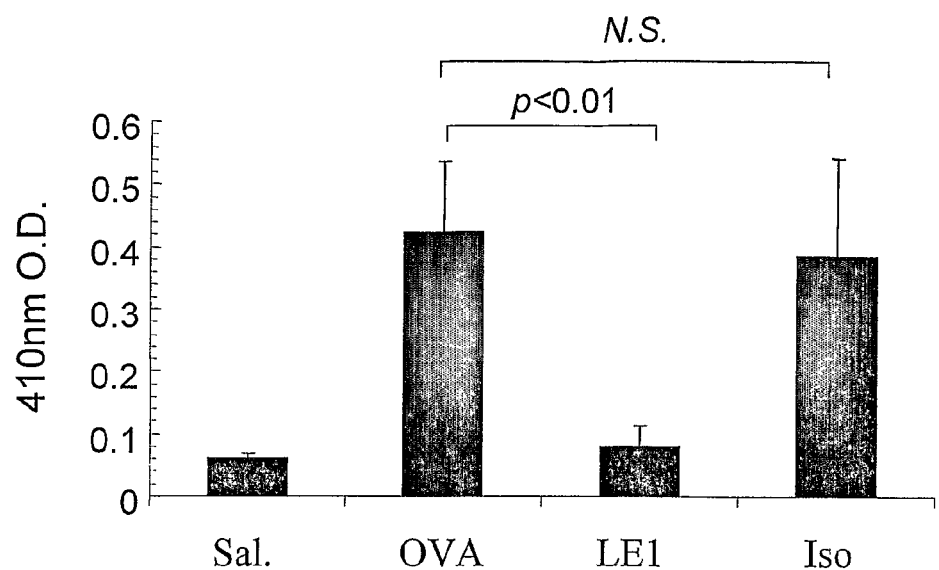
Figure 15B:
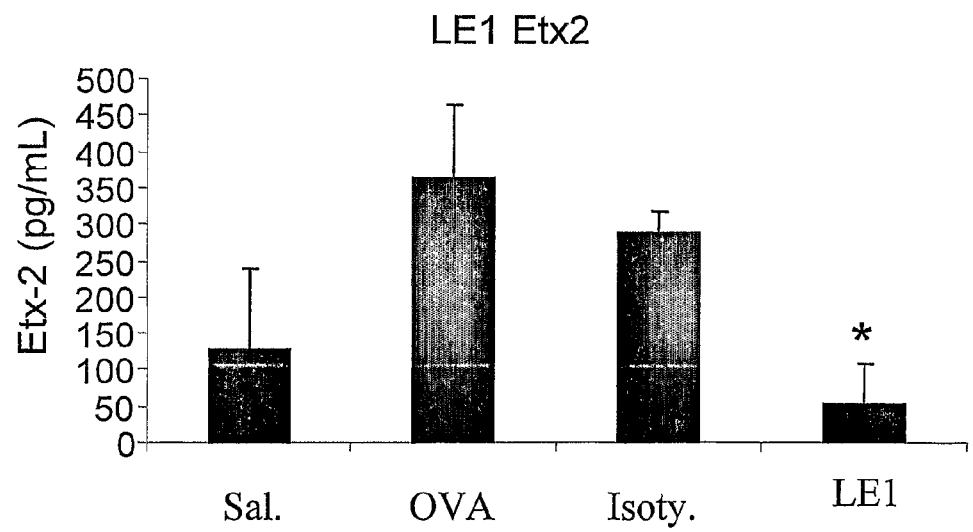

FIGS. 15A-15B: LE1 inhibits tryptase release in a mouse model of allergic peritonitis.

FIG. 15A: Ovalbumin-sensitized mice were injected with 3 μg LE1 or isotype control, followed 30 min later by ovalbumin challenge. 45 min later mice were sacrificed and tryptase was measured in the peritoneal lavage fluid using a chromoenzymatic assay [Sal., saline challenged mice; OVA, ovalbumin challenged mice; LE1, LE1 pretreatment prior to ovalbumin challenge; Iso, isotype pretreatment prior to ovalbumin challenge].

FIG. 15B: LE1 inhibits eotaxin-2 release in a murine model of allergic peritonitis. Ovalbumin-sensitized mice were injected with 3 μg LE1 or isotype control, followed 30 min. later by ovalbumin challenge. 24 hrs later mice were sacrificed and eotaxin-2 was measured in the peritoneal lavage fluid by ELISA [Saline, saline challenged mice; OVA, ovalbumin challenged mice; LE1, LE1 pretreatment prior to ovalbumin challenge; Iso, isotype pretreatment prior to ovalbumin challenge].

Figure 16A:
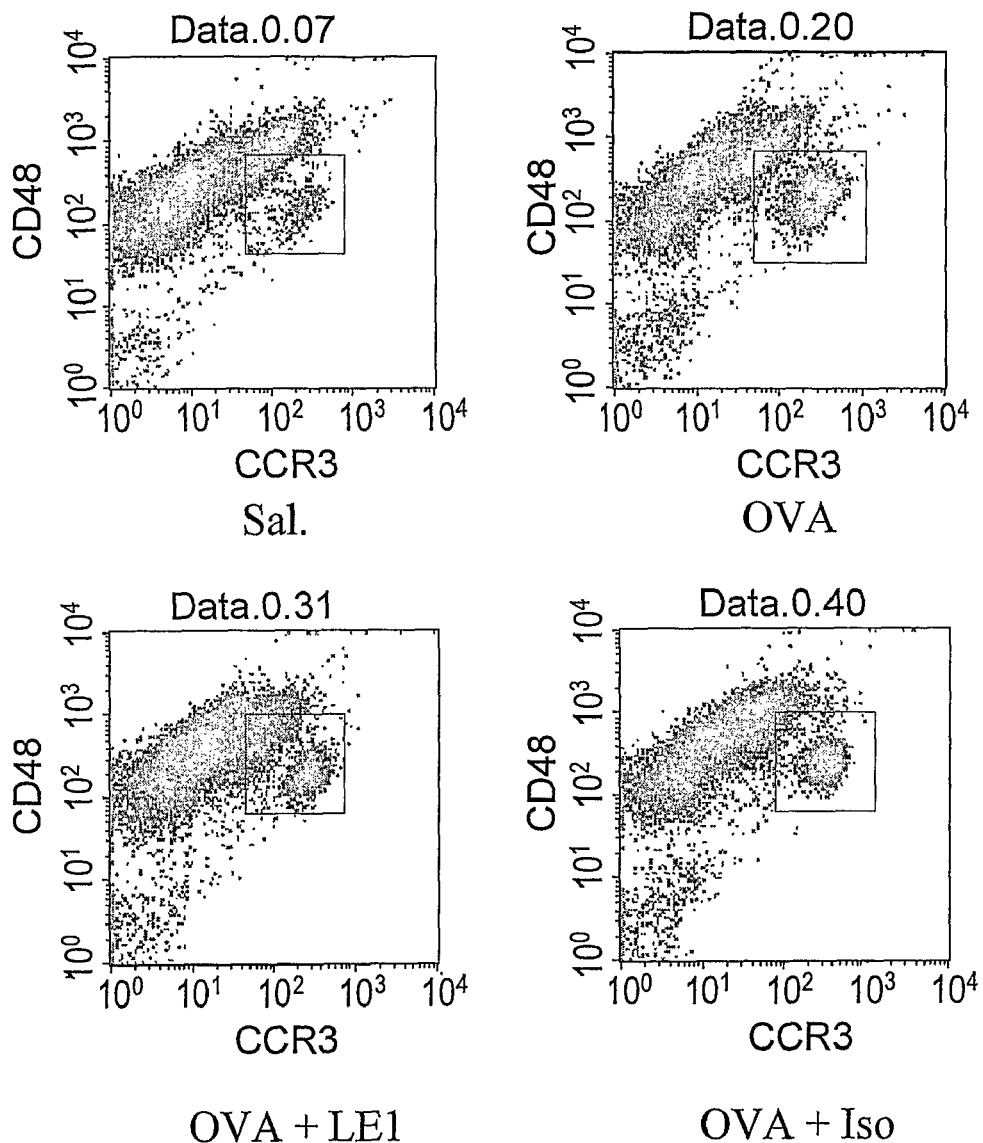
Figure 16B:
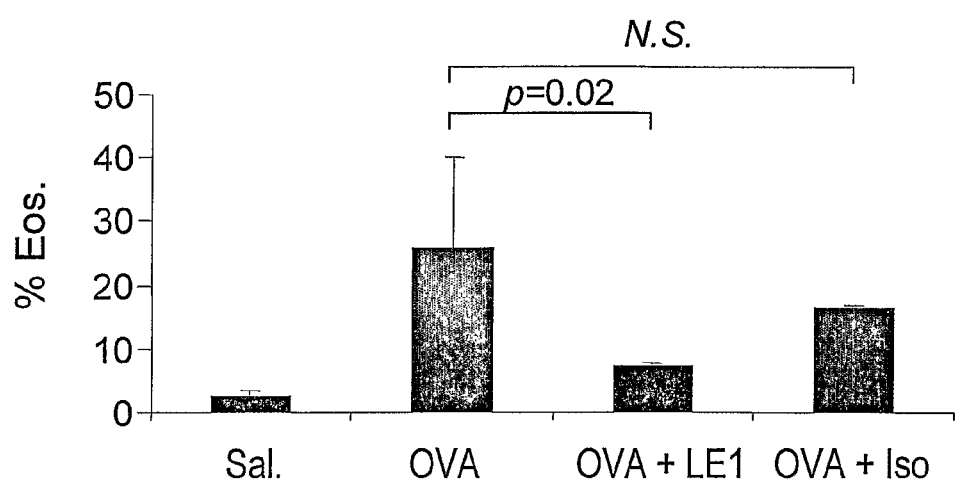

FIGS. 16A-16B: LE1 inhibits eosinophil recruitment in a mouse model of allergic peritonitis.

Ovalbumin-sensitized mice were injected with 3 μg LE1 or isotype control, followed 30 min later by ovalbumin challenge. 48 hr later mice were sacrificed and cells in the peritoneal lavage fluid were normalized to $2\times10^5$ cells and stained for CCR3-FITC and CD48-PE in order to better define the eosinophil population.

FIG. 16A: FACS analysis was performed to quantify the percentage of eosinophils in the peritoneal cavity.

FIG. 16B: Histogram representing the results obtained in the FACS analysis. [Saline, saline challenged mice; OVA, ovalbumin challenged mice; LE1, LE1 pretreatment prior to ovalbumin challenge; Iso, isotype pretreatment prior to ovalbumin challenge].

Figure 17A:
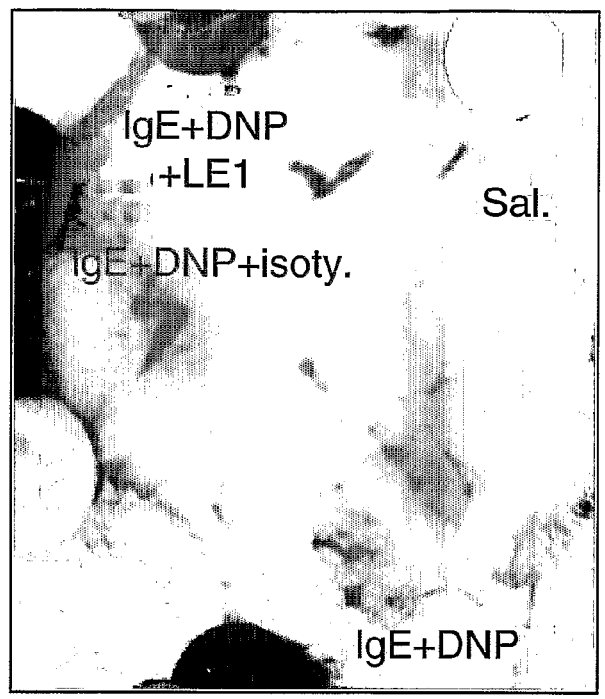
Figure 17B:
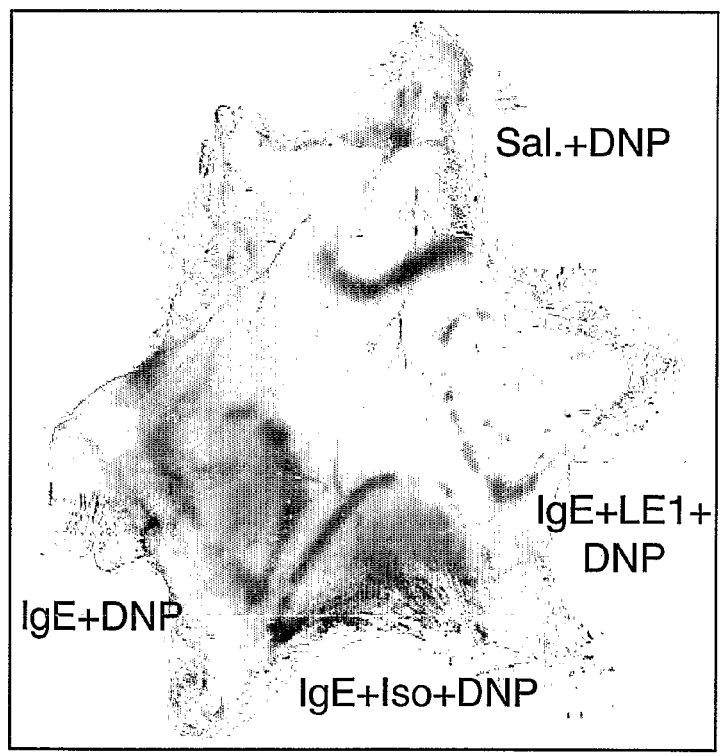

FIGS. 17A-17B: LE1 inhibits mast cell degranulation in a mouse model of passive cutaneous anaphylaxis.

Mice were sensitized with IgE anti-DNP simultaneously with pretreatment with LE1 or isotype control. 2 hr later mice were challenged by intravenous DNP bolus with Evan's blue solution. Cutaneous anaphylaxis was evaluated visually by the blue dye spot size [Saline+DNP, no IgE; IgE+DNP, only IgE; IgE+LE1+DNP, LE1-pretreated site; IgE+isotype+DNP, isotype-pretreated site].

FIG. 17A: Section of skin showing the blue dye spot assay.
FIG. 17B: Same as 17A, different specimen.

DETAILED DESCRIPTION OF THE INVENTION

The following abbreviations are used throughout this specification:
BsAb: bi-specific antibody
CBMC: human cord blood mast cells
ECP: eosinophil cationic protein
FCS: fetal calf serum
HLMC: human lung mast cells
IE1: bi-specific antibody recognizing IRp60 and IgE
ITAM: immunoreceptor tyrosine-based activation motif
ITIM: immunoreceptor tyrosine-based inhibitory motif
LE1: bi-specific antibody recognizing LMIR-1 and IgE
mAb: monoclonal antibody
MAPK: mitogen-activated protein kinase
MBP: eosinophil-derived major basic protein
NGF: Nerve Growth Factor
SCF: Stem Cell Factor
SH2: Src homology 2
Siglecs: sialic acid binding Ig-like lectins While allergy, and particularly asthma, constitutes a major increasing health problem, no efficacious, selective and side-effect-free treatment exists for them as yet.

The present inventors provide a novel approach for allergy and asthma treatment that is virtually free of side effects, and is effective in specifically inhibiting allergic-type reactions as demonstrated in the following Examples. The present invention provides bi-specific complexes which selectively target and inhibit mast cells and eosinophils. By targeting the two key cells involved in the allergic response—mast cells and eosinophils—these bi-specific complexes are useful for every allergen, known or unknown, and for any allergic conditions, e.g. asthma, atopic eczema, allergic rhinitis, allergic conjunctivitis.

Thus, the bi-specific complexes of the invention comprise two different target recognition components. Said components are preferably antibodies or a derivative thereof, e.g. scFv, F(ab), F(ab'), antigen-binding fragment, etc, which are linked via any suitable means. In one particular example, as described in Experimental Procedures ("Bispecific antibody generation"), the recognition components are chemically cross-linked, using as cross-linker 5',5'-dithiobis(2-nitrobenzoic acid) (DNTB), as described [Graziano, R. F. and Guptill, P. (2004) *Chemical production of Bispecific antibodies.* In: *Methods in Molecular Biology.* Vol. 283. Edited by C. M. Niemeyer, Human Press Inc., Totowa, N.J.].

Most importantly, the targets of both recognition components are localized in the same cell. One target is the inhibitory receptor IRp60, or any homologues thereof, e.g. LMIR1, the mouse homologue [Kumagai, H. et al. (2003) *Biochem. Biophys. Res. Commun.*, 307: 719-729]. Binding of the recognition component to the inhibitory receptor triggers an inhibitory pathway which results in the inhibition of the activity of the target cell. The specificity of the complex is provided by the target of the second recognition component, which is always a cell-specific target. One target of choice is, e.g., IgE, which is specifically expressed in mast cells. Other preferred targets which are mast cell specific are cKIT and FcεRI. Similarly, a complex which is directed at eosinophils has a second recognition component which targets e.g. IL-5R or CCR3. In the case of IgE, this immunoglobulin is usually bound to its receptor, FcεRI, and thus the binding of anti-IgE antibody to its target results in the activation of its receptor.

Thus, the bi-specific complexes of the invention are preferably bi-specific antibodies, which target IRp60 and a second target which is specific to mast cells and eosinophils, as well as basophils.

In order to obtain the bi-specific antibodies, the inventors first studied the expression and mechanism of action of IRp60 (see Examples 1 through 11).

IRp60 was originally characterized functionally and molecularly in NK cells [Cantoni, C. et al. (1999) *Eur. J. Immunol.* 29(10): 3148-59], where it was also shown that cross-linking of IRp60 by specific antibodies strongly inhibited NK cell cytotoxicity and cytolytic activity. The present inventors show that cross-linking IRp60 in mast cells inhibits $Ca^{2+}$ influx and mediator release. Similarly, cross-linking IRp60 in eosinophils revealed that this inhibitory receptor regulates eosinophil activation, survival and chemotaxis. It is important to note that the fact that (i) IRp60 is expressed and functional on the effector cells of allergy, and (ii) that it is involved in regulating allergic responses in vivo was totally unexpected, especially because this inhibitory receptor was originally described as unique to lymphocyte/NK populations. Furthermore, the results described herein show that IRp60 is a very potent inhibitory receptor, in contrast to FcγRIIB. This property is likely explained by the fact that IRp60 bears four ITIMs, while FcγRIIB has only one. In addition, IRp60 is the only Ig-superfamily inhibitory receptor that is functional on primary human mast cells and eosinophils. Besides, the in vivo experiments described herein determine the relevance of said inhibitory receptor during allergic inflammation.

Figure 1:
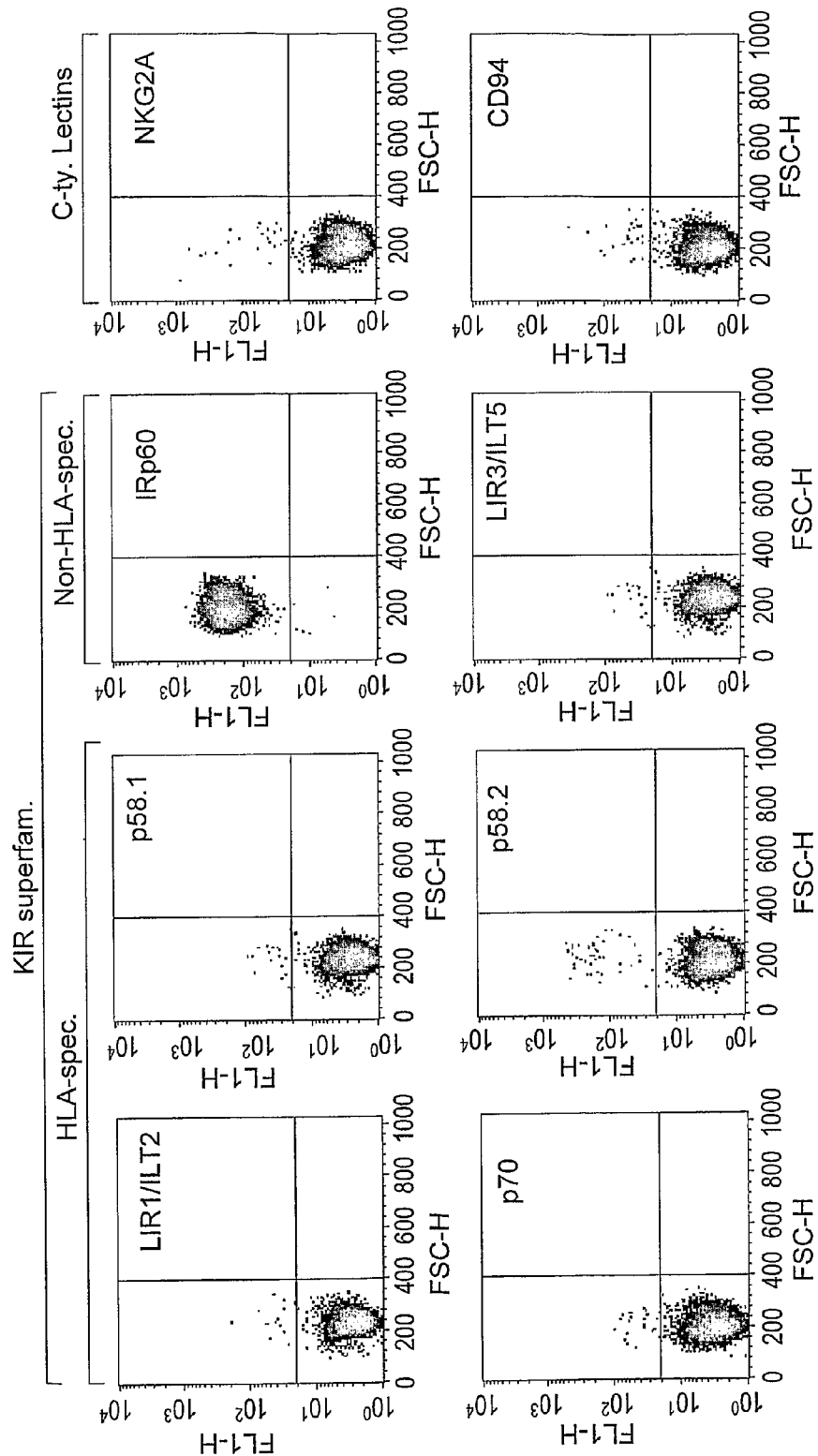
FIG. 1: Screening of human mast cells for inhibitory NK receptors. FACS analysis of a large panel of receptors with known inhibitory function on NK cells revealed that human mast cells express IRp60 in high levels. This expression is unique since other inhibitory receptors were not expressed [n=4].
Figure 1:
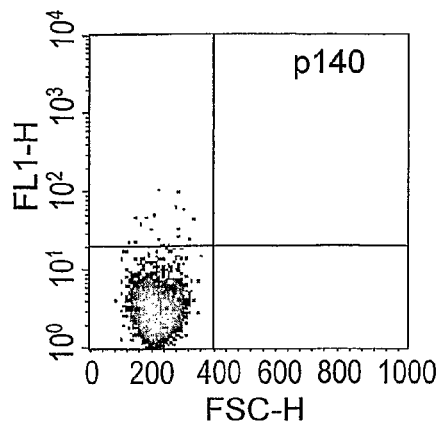
Figure 2A:
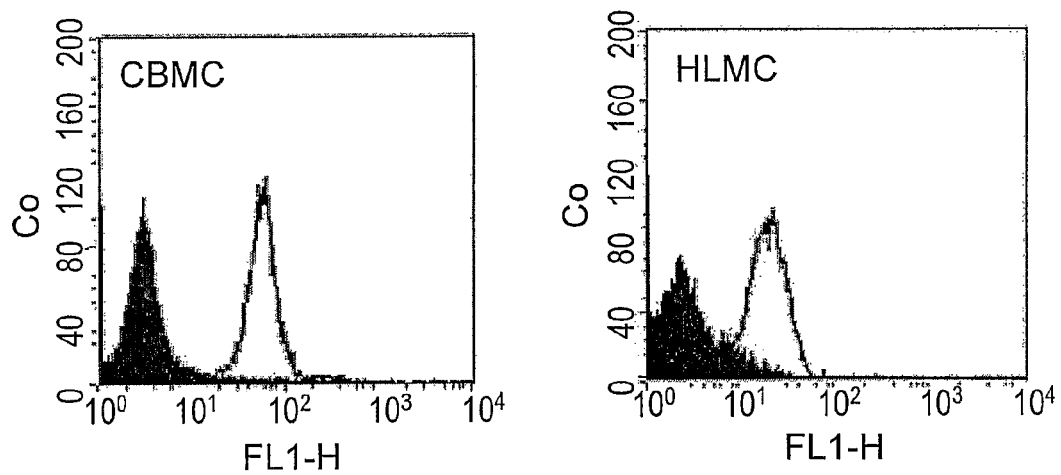
FIGS. 2A-2B: IRp60 is expressed in mast cells and in eosinophils.
Figure 2B:
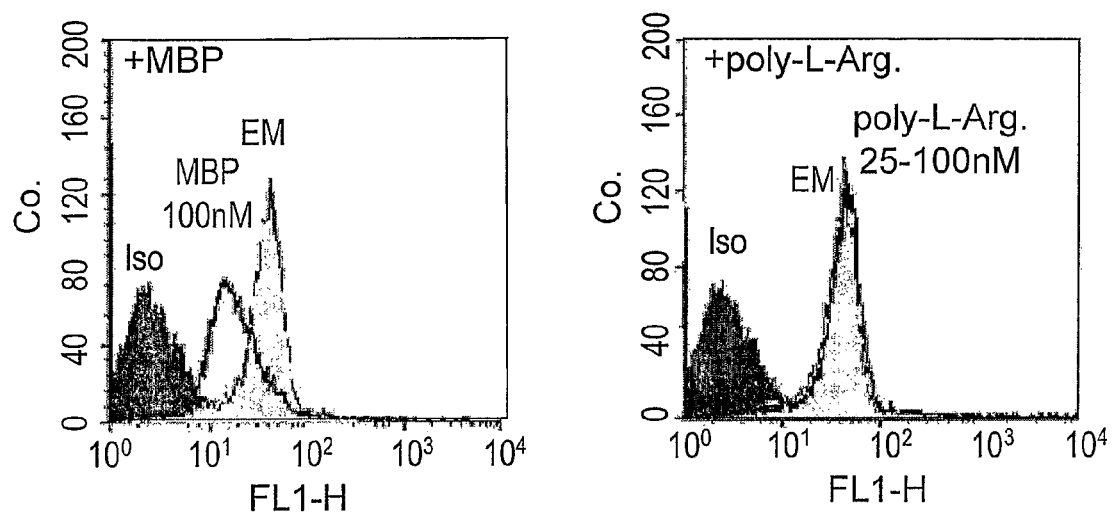

As shown in FIG. 1, IRp60 is expressed on lung tissue mast cells indicating that IRp60 may have a functional significance in mast cell regulation in health and disease. IRp60 is also expressed in NK cells [Cantoni (1999) id ibid.; and data not shown], T cells, monocytes, granulocytes and basophils [data not shown]. Thus, IRp60 may be a potent regulator of various cell types. The expression of IRp60 on mast cells suggests that the response of these cells in the inflammatory milieu may be regulated by this receptor. Indeed, the inventors found that IRp60 expression on mast cells does not change after their culture with various cytokines or mediators [e.g. IL-3, IL-4, IL-13, TNF-α, NGF and monomeric IgE]. FIG. 2 shows that, surprisingly, IRp60 was down-regulated by eosinophil-derived MBP in sub-activating concentrations. Furthermore, MBP induced down-regulation of several receptors, including FcγRIIB, but not of c-kit or FcεRI in IgE-sensitized human mast cells [data not shown]. This finding is extremely important in the context of chronic allergic-inflammation where mast cells and eosinophils interact. Indeed, the inventors and others have shown that MBP can regulate mast cells activation [Piliponsky (2003) id ibid.]. MBP has been shown to activate CBMC co-cultured with fibroblasts, but it does not significantly activate CBMC in suspension in the absence of fibroblasts. It may be hypothesized that MBP regulates mast cells activation thresholds by manipulating the expression of inhibitory receptors. As mentioned before, mast cell activation is most likely kept in a delicate balance between activating signals, mediated through receptors such as FcεRI and c-kit, and inhibitory signals mediated by receptors such as FcγRIIB and IRp60. By decreasing inhibitory signals MBP may shift the balance towards mast cell activation.

Mast cells are known to be activated in allergy mainly through IgE, but they are also able to degranulate upon IgE-independent activation. Therefore, the effect of IRp60 was examined on both modalities. Cross-linking of IRp60 inhibits β-hexosaminidase, tryptase and IL-4 release from IgE-activated CBMC, but not compound 48/80-mediated CBMC activation. This indicates that IRp60 interferes with pathways involving tyrosine phosphorylation, but perhaps not with GTP-dependent G-protein pathways. Additionally it is clear that FcεRI-mediated calcium mobilization, degranulation, and eicosanoid and cytokine synthesis depend on early tyrosine kinase activation events, especially the activation of Syk [Simon M et al (2005) *J. Biol. Chem* 280:4510-7]. Consistent with this, cross-linking of IRp60 was able to block completely the IgE-mediated calcium influx. In addition, cross-linking of IRp60 inhibits the SCF-mediated survival of CBMC. This data is not surprising as several reports have demonstrated the ability of inhibitory receptors to block SCF-mediated effects on mast cells. For example, FcγRIIB was shown to block SCF-mediated survival [Malbec O et al (2002) *Mol. Immunol.* 38:1295-9]. Moreover, gp49B1 was reported to decrease the activation of mast cells via SCF [Feldweg A. M. et al (2003) *Eur. J. Immunol* 33:2262-8]. Taken together, these data allow the prediction of other mast cell functions prone to inhibition by IRp60, but its effect on additional functions, such as pattern recognition through Toll-like receptors and other immune functions has not yet been examined.

Most importantly, the present results were unexpected since the observed mechanism of action of IRp60 differs significantly from that of FcγRIIB in human mast cells in several important aspects. FcγRIIB contains a single ITIM sequence whereas IRp60 contains 4 ITIMs, three of which are canonical (following the I/S/L/V-x-Y-x-x-L/V consensus) while the fourth is not [Cantoni (1999) id ibid.]. The actual role of this ITIM as a docking site for consequent phosphatase recruitment is still unclear, although it can undergo tyrosine phosphorylation [data not shown]. Another difference is that IRp60 has been shown to recruit only SHP-1 and SHIP-1, but not SHP-2. This observation supports recently reported data in which IgSF13, a close family member of IRp60, follows the same phosphatases deployment pattern [Sui L. et al (2004) *Biochem Biophys. Res. Commun* 319:920-8]. Although the possibility of differential phosphatase recruitment by various inhibitory receptors exists, the meaning of this result still needs to be investigated.

The bispecific antibodies described in the present invention, or compositions comprising thereof, are thus designed to selectively activate an inhibitory mechanism (pathway) on mast cells and eosinophils, the two key effector cells of allergy, thus, selectively triggering inhibitory pathways in these target cells only. Said inhibition is done through the inhibition of their function or activity, as detailed below.

As mast cell or eosinophil activity (or function) it is understood any one of the following processes: maturation, survival, degranulation, priming (preparing the cell for action, alerting it to standby), chemotaxis, adherence, proliferation and synthesis of cytokines, growth factors, arachidonic acid metabolites, chemokines, phospholipid metabolites and others. Activation of these processes depends on the stimulation (i.e. induction or activation) of a receptor, which is specific to these cells. Furthermore, any of these processes may be used as a parameter for determining the capacity of the bi-specific complex to inhibit mast cells or eosinophils activity, and to treat conditions induced by allergic-type reactions and mast cell/eosinophil-mediated reactions.

Thus, the inhibitory pathway which is activated through the binding of the bi-specific complex (e.g. the bi-specific antibody described in the invention), to its two targets—the inhibitory receptor IRp60 and the second, activator target—may be described by the following cascade of events, which happen consecutively or concomitantly: (a) phosphorylation of the intracellular ITIM domains of the inhibitory receptor; (b) recruitment of intracellular phosphatases, e.g. SHP-1, SHP-2, SHIP-1, SHIP-2, or PTEN; (c) dephosphorylation of ITAM or tyrosine phosphorylation domains present in the activator target.

Hence, the bispecific antibody described herein may be used in vivo or ex vivo in the treatment of allergic-type reactions and mast cell/eosinophil-mediated reactions, and any condition derived from mast cell/eosinophil hyperactivity or hyperplasia.

In order to investigate the biological relevance of IRp60 activation in vivo, the inventors neutralized this receptor in a murine model of allergic peritonitis (Examples 7 and 14). IRp60 is an allelic isoform of CMRF-35H [Cantoni C et al. (1999) *Eur. J. Immunol.* 29-3148-59]. Since no in vivo function has been attributed to IRp60 as yet, a murine CMRF-35H family member [termed CLM-1] was shown to inhibit osteoclast formation through SHP-1 recruitment [Chung, D. H. et al. (2003) *J. Immunol.* 171(12):654'-8]. It has been recently reported that murine mast cells express an Ig-superfamily receptor termed LMIR1 [Kumagai (2003) id ibid.] which is 80% identical to human IRp60, with the important functional residues in the V-type Ig-fold and ITIM sequences well conserved, and is able to recruit SHP-1 and -2 via tyrosine phosphorylation. The present results indicate that neutralization of LMIR1 enhances tryptase and β-hexosaminidase levels in the peritoneal lavage of LMIR1 treated mice. In addition, the consequent eosinophilic inflammation was augmented. This indicates that IRp60 (and its yet undefined ligand) have a role in allergic settings in vivo as well.

Finally, in order to examine the effect of the cross-linking of IRp60 and IgE both in vitro and in vivo, the inventors have generated two sets of bispecific constructs (IE1, bi-specific anti-IRp60-anti-IgE; LE1, bi-specific anti-LMIR1-anti-IgE) and their matching isotype controls. IE1 inhibited IgE-mediated degranulation of human mast cells in vitro, while LE1 inhibited the release of tryptase and eotaxin-2, and the eosinophilic infiltration in a murine model of allergic peritonitis. Moreover, LE1 inhibited cutaneous anaphylaxis in a murine PCA model. This proves that cross-linking of IRp60 and IgE (or LMIR1 and IgE) is an efficient way to inhibit mast cell and eosinophil function and activity in allergic-inflammatory settings.

As used herein in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

The pharmaceutical composition used by the method of the invention can be prepared in dosage units forms and may be prepared by any of the methods well-known in the art of pharmacy. In addition, the pharmaceutical composition may further comprise pharmaceutically acceptable additives such as pharmaceutical acceptable carrier, excipient or stabilizer, and optionally other therapeutic constituents. Naturally, the acceptable carriers, excipients or stabilizers are non-toxic to recipients at the dosages and concentrations employed.

The magnitude of therapeutic dose of the composition of the invention will of course vary with the group of patients (age, sex, etc.), the nature of the condition to be treated and with the route administration, all of which shall be determined by the attending physician.

The pharmaceutical compositions of the invention may be administered systemically, for example by parenteral, e.g. intravenous, intraperitoneal or intramuscular injection. Alternatively, the pharmaceutical composition can be delivered by any suitable route, including subcutaneous, transcutaneous, topical, intraarticular, subconjunctival, or mucosal, e.g. oral, intranasal, inhaled or intraocular administration. Local administration to the area in need of treatment may be achieved by, for example, local infusion during surgery or topical application.

For oral administration, the pharmaceutical preparation may be in liquid form, for example, solutions, syrups or suspensions, or in solid form as tablets, capsules and the like. For administration by inhalation, the compositions are conveniently delivered in the form of drops or aerosol sprays. For administration by injection, the formulations may be presented in unit dosage form, e.g. in ampoules or in multidose containers with an added preservative.

Thus, the bispecific antibodies of the invention have two main therapeutic and financial advantages that go side by side. First, it is not allergen specific, thus it could be used in patients allergic to more than one allergen and even if the allergen(s) is unknown as it frequently happens in clinical settings. Second, in future therapeutic uses it can be delivered topically by sprays, creams, eye and nose drops etc and not by the cumbersome intravenous route. Intravenous routes are also hopefully avoided because (1) there is a higher risk for side effects; (2) pharmacokinetically, the drug half-life is shorter, usually because the drug will be cleared off, excreted, disintegrated etc.; and (3) significantly less drug is needed if administered locally.

The amount of the therapeutic or pharmaceutical composition of the invention which is effective in the treatment of a particular disease, condition or disorder will depend on the nature of the disease, condition or disorder and can be determined by standard clinical techniques. In addition, in vitro assays as well in vivo experiments may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. The amount must be sufficient to inhibit the one of the processes that enable a mast cell or an esinophil to trigger an allergic-type reaction. For the murine model described herein, 3 μg of the bispecific antibody LE1 was sufficient to induce said response, which is the equivalent of about 27 pmole.

As used herein, "effective amount" means an amount necessary to achieve a selected result. For example, an effective amount of the composition of the invention useful for inhibition of mast cell or eosinophil activity and thereby for the treatment of allergic-type reactions, as well as mast cell and/or eosinophil and/or basophil-mediated reactions.

It should be appreciated that the antibody of the invention may be a polyclonal or a monoclonal antibody.

The generation of polyclonal antibodies against proteins is described in Chapter 2 of Current Protocols in Immunology, Wiley and Sons Inc.

Monoclonal antibodies may be prepared from B cells taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology. Spleen or lymph node cells of these animals may be used in the same way as spleen or lymph node cells of protein-immunized animals, for the generation of monoclonal antibodies as described in Chapter 2 therein. The techniques used in generating monoclonal antibodies are further described in by Kohler and Milstein [Kohler and Milstein (1975) *Nature* 256; 495-497] and in U.S. Pat. No. 4,376,110.

Fab and F(ab')$_2$ and other fragments of antibodies are typically produced by proteolytic cleavage, using enzymes such as papain (to produce Fab fragments) or pepsin (to produce F(ab')$_2$ fragments).

Structurally, the bi-specific antibodies described in the present invention may be defined as follows. A synthetic F(ab')$_2$ fragment (i.e., a conjugate of 2 F(ab') fragments, each recognizing a different determinant), generated by a three step process: (1) treating mouse or rat whole IgG molecules (specific to each one of the targets of interest, as defined herein) with pepsin, thus generating F(ab')$_2$ fragments; (2) reducing each F(ab')$_2$ through treatment with 2-mercaptoethylamine, generating F(ab') fragments; and (3) re-conjugating the F(ab') fragments of each antibody with the other, B thus generating the bispecific hybrid F(ab')$_2$. Thus, said bi-specific antibody is in all aspects a complete F(ab')$_2$ molecule, ~110 KDa in weight, considering that a F(ab')$_2$ molecule is defined as the product of pepsin treatment of an IgG molecule.

For future clinical applications, the bi-specific of the invention may be improved through a humanization process, to overcome the human antibody to mouse antibody response. Rapid new strategies have been developed recently for antibody humanization which may be applied for such antibody. These technologies maintain the affinity, and retain the antigen and epitope specificity of the original antibody [Rader, C. et al. (1998) *Proc. Natl. Acad. Sci. USA*, 95: 8910-8915; Mateo, C. et al. (1997) *Immunotechnology* 3: 71-81]. Unlike, for example, animal derived antibodies, "humanized" antibodies often do not undergo an undesirable reaction with the immune system of the subject.

Thus, as used herein, the term "humanized" and its derivatives refers to an antibody which includes any percent above zero and up to 100% of human antibody material, in an amount and composition sufficient to render such an antibody less likely to be immunogenic when administered to a human being. It is being understood that the term "humanized" reads also on human derived antibodies or on antibodies derived from non human cells genetically engineered to include functional parts of the human immune system coding genes, which therefore produce antibodies which are fully human.

In sum, the bispecific antibodies described herein represent a novel approach for the down modulation of mast cell and eosinophil effector functions in allergic inflammatory diseases in general and in mast cell/eosinophil-related diseases, such as allergic asthma, allergic rhinitis, seasonal allergic conjunctivitis, atopic dermatitis and atopic eczema, allergic disorders and responses to various allergens, systemic anaphylaxis, systemic mastocytosis, morphea/urticaria pigmentosa, mast cell leukemia, atherosclerosis, graft rejection, multiple sclerosis, fibrotic lung diseases, neurofibromatosis, keloids, scleroderma, rheumatoid arthritis, osteoarthritis, acute gout, ocular cicatricial pemphigoid, Crohn's disease, peritoneal adhesions, chronic graft versus host disease (GVHD), eosinophil myalgia syndrome, extrinsic bronchial asthma, nasal polyposis, Wegener's granulomatosis, intrinsic bronchial asthma, interstitial and other pulmonary diseases, chronic eosinophilic pneumonia, hypersensitivity pneumonitis, allergic bronchopulmonary aspergillosis, sarcoidosis, idiopathic pulmonary fibrosis, toxocariasis, filariasis, schistosomiasis, trichinosis, neoplastic and myeloproliferative diseases, T cell lymphomas and Hodgkin's disease.

One particular population that might profit from the present invention is that of individuals that suffer from mastocytosis. Mastocytosis is a group of disorders characterized by the presence of too many mast cells in the body. It may be cutaneous or systemic. The excess mast cells and their signaling results in bone and muscular pain, abdominal discomfort, nausea and vomiting, stomach ulcers, diarrhea, skin lesions, episodes of very low blood pressure and faintness and shock. So far there is no specific treatment for mastocytosis. Treatment is usually based in anti-histamines or medicines to relieve the symptomatic manifestations of the disease. However, no mast cell-specific treatment has been found. Thus, the bispecific antibodies of the invention that target mast cells, or compositions comprising thereof, are the ideal agent to be used for the treatment of said disease.

Conditions mediated by the activation of basophils are also potential targets to be treated with the bi-specific antibodies of the invention, since these cells are thought to play functions overlapping with those of mast cells. Basophils exhibit many characteristics in common with mast cells, especially the expression of the high affinity IgE receptor FcεRI, and a high content of histamine and granule-stored tryptase. Moreover, basophils express high levels of IRp60 (inventors' data not shown). Since basophils IgE-dependent activation can be inhibited by the inhibitory receptor FcγRIIB, it is very likely that binding of the bi-specific antibody to IRp60/IgE shall also trigger the inhibitory pathway in these cells. Particular conditions that may be treated with the bi-specific antibodies of the invention are anaphylactic response to contrast media, anaphylactic response to muscle relaxants and basophilic leukemias.

The potential of the bispecific antibodies described herein may even exceed the scope discussed above. Given the proper effector mechanisms on other cells, it is conceivable that other diseases such as autoimmune diseases, where pinpoint targeting of specific cell types is desired, could be treated.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Antibodies and Reagents

All the cell culture media, reagents and buffers were purchased from Biological Industries, Beit Haemek, Israel. SCF is a kind gift from Amgen, Inc. [Thousand Oaks, Calif., USA]. The following mAbs recognizing various inhibitory receptors were produced by standard procedures described in the literature and used: P192 and E59 [anti-IRp60], XA-185 [anti-CD94], 11PB6 [anti-p58.1], GL183 [anti-p58.2], Z27 [anti-p70], Q66 [anti-p140], AZ158 [anti-p70/p140], F278 [anti-LIR1/ILT2]. The antibody recognizing LIR3/ILT5 [15F3] was kindly provided by Colonna M., Washington University, St Louis. Anti-LMIR1 was purchased from R&D Systems [Minneapolis, Minn., USA]. Anti-human CD117 antibody for human lung mast cell purification was purchased from BD-Pharmingen [San Diego, Calif., USA]. Anti-human tryptase [clone AA1] and isotype control [IgG1 and IgG2A] antibodies were purchased from Dako [Glostrup, Denmark]. Sheep anti-mouse $F[ab']_2$ antibody was purchased from ICN Biomedicals [Aurora, Ohio, USA]. Chimaeric murine/human IgE anti-NP antibody was purchased from Serotec [Raleigh, N.C., USA]. Goat anti-mouse X-chain specific antibody was purchased from Southern Biotech [Birmingham, Ala., USA]. Polyclonal anti-human phosphotyrosine [pY99], SHP-1/2 and SHIP-1 antibodies were purchased from Santa Cruz [Santa Cruz, Calif., USA]. Horseradish peroxidase-conjugated anti-rabbit and anti-mouse, fluorescein isothiocyanate [FITC]-, $Cy^5$- and phycoerythrin-conjugated anti-mouse antibodies were all purchased from Jackson Laboratories [West Grove, Pa., USA]. Chromogenic substrates were purchased from Sigma [St. Louis, Mo., USA]. Calcium Green-1AM was purchased from Molecular Probes [Eugene, Oreg., USA]. Ficoll-paque was purchased from Amersham Biosciences [Uppsala, Sweden]. All other reagents were purchased from Sigma, unless otherwise stated, and were of best chemical grade available.

Bispecific Antibody [BsAb] Generation

Bispecific F(ab')2 fragment deriving from whole mouse or rat IgG antibodies recognizing separate epitopes was generated basically as described by Brennan and Graziano with slight modifications. Mouse anti-human IgE and anti-human IRp60 were digested using immobilized pepsin beads according to the manufacturer's protocol as described for 4 hr at 37° C. in a shaking bath. F(ab')2 fragments were purified using centrifugal gel filtration on a vivaspin column, and reduced to Fab' fragments by incubating in reduction buffer [1 mM EDTA, 1 mM 2-mercaptoethylamine, 10 mM sodium arsenite, 0.1M sodium phosphate, pH 6.8] overnight at 25° C. To the anti-IRp60 only, 5',5-dithiobis[2-nitrobenzoic acid] [Ellman's Reagent] was added to a final volume of 10 mM, and incubation was continued for 4 hr at 25° C. Both antibodies were then cleaned by gel filtration, transferred to coupling buffer [1 mM EDTA, 0.1M sodium phosphate, pH 6.8], mixed and incubated overnight at 25° C. The resulting F(ab')2 was purified by gel filtration, recovered in PBS and quantified using spectrophotometry. The specificities were evaluated by FACS. For mouse IgE and LMIR1, rat IgG underwent the same process except for 5 hr incubation with immobilized pepsin. BsAbs recognizing the following target sets were created: IE1 [hIgE-IRp60], hIgE-Isotype [control], LE1 [mIgE-LMIR1], mIgE-Isotype [control].

Methods for Assays with Mast Cells a. Mast Cell Purification and Culture

It is noteworthy that most of the knowledge on mast cells to date relies on studies performed on rodent mast cells and human mast cell lines. In the inventors' laboratory, which focuses on human therapy, the technology to purify and culture specifically human mast cells from cord blood, lung, skin and intestine has been developed.

Thus, human cord blood mast cells [CBMC] were obtained by culturing umbilical cord blood mononuclear precursors as previously described [Piliponsky (2003) id ibid.]. Briefly, fresh cord blood was diluted with Hank's solution, loaded on Ficoll-Paque and centrifuged [350×g, 25 min]. Mononuclear cells were washed twice with Hank's and resuspended with 100 mL Minimum Essential Medium [MEM]-Alpha containing 10% v/v heat inactivated foetal calf serum [FCS], penicillin [100 U/mL], streptomycin [100 μg/mL], ribonucleosides/deoxyribonucleosides, SCF [100 ng/mL], IL-6 [10 ng/mL] [Peprotech, Rocky Hill, N.J., USA] and $PGE_2$ [0.3 μM] [Sigma]. The culture medium was replaced weekly. CBMC were used after 8-12 weeks of culture, when >97% of the cells were positive for tryptase as assessed by intracellular flow cytometry [FACS, see below]. Human lung mast cells [HLMC] were purified from healthy-looking lung specimens surgically removed from lung cancer patients, using proteolysis, gradient and positive magnetic sorting as described [Piliponsky AM. et al. (2003) id ibid.]. Lung samples and cord blood were obtained according to the Institutional Helsinki Committee guidelines of the Hadassah Medical School (Jerusalem, Israel) and their use was approved by the committee.

b. Flow Cytometry [FACS]

Flow cytometry was performed using Becton-Dickinson FACScalibur and CellQuest software. All stages were performed in a round-bottom 96-well culture plate [Nunc, Roskilde, Denmark] in a volume of 100 μL. Most cells [~$10^5$/sample] were washed with ice-cold HBA buffer [Hank's solution containing BSA [0.1% w/v] and $NaN_3$ [0.01% w/v]], then incubated with either anti-IRp60 or the appropriate isotype control [4° C., 30 min] followed by two washes with cold HBA. The cells were then incubated with secondary antibodies [FITC- or $Cy^5$-conjugated anti-mouse at the recommended dilutions, 4° C., 30 min] followed by two additional washes, and analyzed immediately by FACS. Intracellular FACS was performed essentially the same, except for the two stages prior to the addition of the primary antibody. In this case the cells were first fixed in 2% formaldehyde [4° C., 10 min] and blocked with HBA containing BSA [10% w/v], goat serum [0.1% v/v], saponin [0.1% w/v] and HEPES [10 mM] [4° C., 10 min]. HBA containing saponin [0.1% w/v] and HEPES [10 mM] was also employed for incubation and washing.

c. Mast Cell Activation and Inhibition

Five days prior to activation, CBMC were incubated with chimeric murine/human IgE anti-NP antibody [5 μg/mL]. For activation, an Immunolon-2HB 96-well plate [ThermoLabsystems, Franklin, Mass., USA] was incubated with or without sheep anti-mouse $F[ab']_2$ [25 μg/mL in PBS] [37° C., 4 hr], followed by 2 washes with PBS. Next the plate was incubated with anti-IRp60 [20 μg/mL], isotype control or PBS [37° C., 4 hr] and washed twice with PBS. On the day of activation, cells [$2\times10^5$ cells/sample] were washed twice in warm Tyrode's gelatin-calcium buffer [137 mM NaCl, 12 mM NaHCO$_3$, 5.5 mM L-Glucose, 2 mM KCl, 0.3 mM Na$_2$HPO$_4$, 0.1% w/v gelatin, 1.8 mM CaCl$_2$, 0.9 mM MgCl$_2$] supplemented with SCF [100 ng/mL]. The cells were then transferred to the coated plate, and either anti-mouse IgE λ-chain specific antibody [5 μg/mL] or compound 48/80 [10 μg/mL] were added, and the cells were incubated for 30 min at 37° C. Finally, the cells were immediately centrifuged [1500×g, 1 min], separated from the supernatant and lysed by 3 freeze/thaw cycles. Supernatant and lysate were recovered and stored at −80° C. until assessed for the amounts of mediators released.

d. Mediator Release Assays

β-hexosaminidase and tryptase were measured by chromogenic assays as described [Woolhiser, M. R. et al. (2004) *Clin. Immunol.* 110(2):172-80; Greenfeder S. et al. (2003) *Biotechniques* 34(5):910-2, 914] with slight modifications. For β-hexosaminidase, 18 μL of sample [supernatant or cell lysate] were mixed with 42 μL of substrate solution [8 mM p-nitrophenyl-N-acetyl-β-D-glucosaminide in 48 mM citric acid and 56 mM Na2HPO4, pH 4.5] and incubated for 2 hr at 37° C. The reaction was stopped by addition of 120 μL ice-cold glycine [0.2M] pH 10.7 and the O.D. was immediately read in a standard spectrophotometer at 410 nm absorbance. For tryptase, 48 μL of sample were thoroughly mixed with 2 μL of substrate solution [25 mM N-p-tosyl-gly-pro-lys-p-nitroanilide in 100% DMSO], incubated at 37° C. until chromogenesis and immediately read as above. Percent release was calculated using the following formula: % R=100× Supernatant/[Lysate+Supernatant] within the linear range of the O.D. curve. IL-4 release was measured by a commercial ELISA kit [Diaclone, Besancon, France].

e. Survival Assay

CBMC [$2\times10^5$ cells/sample] were washed with MEM-Alpha without growth factors, and incubated in 200 μL MEM-Alpha with or without SCF [100 ng/mL] in a culture plate coated as described above. At 24 and 48 hr samples were stained by addition of 5 μL with propidium iodide solution in PBS [10% v/v] and immediately analyzed by FACS.

f. Modulation of Receptor Expression

CBMC [$3\times10^5$ cells/sample] were cultured in the presence of either TNF-a [20 ng/mL], IL-3 [20 ng/mL], IL-4 [20 ng/mL], NGF [50 ng/mL] [all purchased from Peprotech, Rocky Hill, N.J., USA], chimeric IgE [5 μg/mL] [Serotec], eosinophil MBP [0.01-0.1 μM], purified as described [Piliponsky (2003) id ibid.], or poly-L-arginine [25-100 nM] for 0, 4, 12 and 24 hr at 37° C. At these time points IRp60 expression was assessed by FACS.

g. Intracellular Ca$^{2+}$ Mobilization

Prior to loading with calcium sensor, IRp60 on CBMC [$3\times10^5$ cells/sample] was cross-linked by incubation with anti-IRp60 or isotype [10 μg/mL, 30 min on ice], followed by washing and incubation with sheep anti-mouse F[ab']2 [25 μg/mL, 30 min on ice] in MEM-Alpha. The cells were loaded with Calcium Green-1AM [5 μm, 45 min, 37° C.] in MEM-Alpha [FCS, 2% v/v], washed and suspended in 400 μL Tyrode's gelatin-calcium buffer warmed to 37° C. The cells were allowed to flow freely in the cytometer for 100 sec, at which time anti-IgE [5 μg/mL] was added. Changes in FL-1 geo mean were recorded for a total of 5 min.

h. Immunoprecipitation and Western Blot

CBMC were lysed using a commercial lysis buffer [Pierce, Rockford, Ill., USA], run on 10% SDS-PAGE, transferred to PVDF membranes [Pierce] and blotted vs. IRp60 [anti-IRp60, 1 μg/mL]. For IRp60 precipitation, CBMC [$8\times10^6$ cells/sample] were treated with sodium orthovanadate [4mM, 10 mins, 37° C.] or incubated in a coated plate for various time periods. IRp60 was precipitated from CBMC using a commercial kit [Seize™ Classic Mammalian kit, Pierce] according to the manufacturer's instructions. The samples were run as described and blotted vs. phosphotyrosine [pY99], SHP-1/2 and SHIP-1. For detection, horseradish peroxidase conjugated anti-mouse or anti-rabbit antibodies were used as recommended by the manufacturer.

Methods for Assays with Eosinophils a. Eosinophil Purification

Eosinophils were purified from the peripheral blood of mildly atopic individuals (blood eosinophil levels, 5-10%). Written informed consent was obtained from all volunteers according to the guidelines established by the Hadassah-Hebrew University Human Experimentation Helsinki Committee. Briefly, venous blood (50-100 ml) was collected in heparinized syringes and left to sediment in 6% dextran (Amersham Biosciences). Leukocytes were centrifuged on Ficoll-Hypaque (density, 1.077; 25 min, 700 g, 22° C.; Amersham Biosciences). Neutrophils and contaminating lymphocytes were tagged in the granulocyte-enriched pellet with micromagnetic beads bound to anti-CD16 and anti-CD3 Abs (Miltenyi Biotec). Eosinophils were purified by passing the cell suspension through a magnetic column (MACS). Cells were collected at a purity of at least 98% by Kimura staining, with a viability of at least 98% by trypan blue staining. No CD56+ or CD3+ cells were observed in the contaminating fractions, by FACS analysis (data not shown).

b. Flow Cytometry

For flow cytometry (FACS) analysis, cells ($1\times10^5$) were incubated in 15% human serum (to block FcRs) in a final volume of 100 μl of HBSS supplemented with 0.1% BSA and 0.02% sodium azide (HBA) for 30 min on ice. Eosinophils were cultured with different Abs recognizing inhibitory receptors, followed by goat anti-mouse FITC Abs (1/200). For survival experiments Annexin-PI staining was performed using the R&D Annexin-PI kit according to the manufacturers' instructions.

After staining, the cells were analyzed on a FACSCalibur system (BD Biosciences). For each staining, at least 10,000 events were collected, and data analysis was performed using CellQuest software (BD Biosciences)

c. Cell culture and Activation

Ninety-six well plates (Nunc) were precoated with sheep anti-mouse F(ab')2 in PBS (25 μg/ml, 2 h, 37° C., 5% CO2). Afterward, plates were washed three times with PBS and incubated with P192 (anti-IRp60) or irrelevant isotype-matched control Ab (1-5 μg/ml, 2 h, 37° C., 5% CO2) and washed again three times. Freshly isolated eosinophils were seeded in these precoated wells ($2\times10^5/200$ μl) in medium containing RPMI 1640, 200 U/ml penicillin, 200 μg/ml streptomycin, and 5% (v/v) heat-inactivated FCS (enriched medium (EM)), and IL-5 or GM-CSF at different concentrations was added (1-100 ng/ml). The cells were incubated for 18-24 hrs (37° C., 5% CO2). At the end of the incubation, cells were centrifuged (250 g, 5 min, 4° C.), and supernatants were collected, aliquoted, and stored at −80° C. until assessed for cytokines or fibroblast proliferation assays.

For survival assays, the cells were activated in suspension as follows: P192 (anti-IRp60) or irrelevant isotype-matched control Ab was added to the cells ($2\times10^5$, 1-5 μg/ml, 30 min, 4° C.). Cells were washed and sheep anti-mouse F(ab')2 was added (25 μg/ml, 30 ml, 4° C.). Thereafter the cells were washed three times (250 g, 5 min, 4° C.) and IL-5 or GM-CSF was added (1-100 ng/ml) for different time points (12-48 hrs). Viability was assessed by flow cytometry as described above.

d. Cytokine Determination

IL-8 was quantified in the eosinophil culture supernatants using DuoSet (R&D Systems). The lower limits for assay sensitivity was 7 pg/ml for IL-8. IL-1b, IFN-γ and IL-4 were detected using the FlowCytomix kit detecting 10 different cytokines according to the manufacturers' instructions.

e. Chemotaxis Assay

Eosinophil migration was measured using a microwell dual chamber system (ChemoTx chamber: filter pore size 5 μm, 6.0 mm diameter wells; Neuro Probe Inc. Gaithersburg, Md.). Recombinant human eotaxin (1-100 ng/ml) was added in triplicates to wells in the bottom chamber and covered with a framed filter. Next, eosinophil suspensions that were activated by anti-IRp60 or isotype matched control (30,000 cells/30 μl) were placed on top of the filter over each well and the chamber system was incubated for 90 min (37° C., 5% CO2). After incubation, the non-migrated eosinophil suspension on top of the filter was removed using tissue paper and the cells in the lower chamber were counted by flow cytometry (FACScalibur, Beckton Dickinson). Briefly, relative cell counts were obtained by acquiring events for 60 seconds.

f. Shape Change Assay

Eotaxin-induced eosinophil shape change was assessed by using flow cytometric analysis. Eosinophil suspensions that were activated by anti-IRp60 or isotype matched control were incubated with recombinant human eotaxin (1-100 ng/ml) for 5-10 min (37° C., 5% CO2). Thereafter, the cells were washed and analyzed by means of flow cytometry (FACScalibur, Beckton Dickinson) and the FSC of 10,000 cells was acquired.

g. Fibroblast Proliferation Assay

Proliferation of the sub-confluent fibroblast monolayer was assessed by [$^3$H]-thymidine incorporation. Fibroblasts were seeded in 96-well plates ($5\times10^3$ cells/well) in 200 ml of supplemented DMEM/10% FCS overnight, washed twice with supplemented DMEM/0.5% FCS, and stimulated with supernatants of eosinophils that were activated by IRp60 or isotype matched controls for 24 hr. [$^3$H]-thymidine (NENTM Life Science Products, Inc., Boston, Mass.) was added as a final 24-hr pulse (1 μCi/well), and samples were processed as described previously.

Animals and Allergic Peritonitis Model

Allergic peritonitis was induced in 8-10 weeks old female BALB/c mice using ovalbumin [OVA] as described [Zuany-Amorim et al. (1994) *Ann NY Acad Sci* 725:34-43]. Briefly, on days 0 and 7 mice were sensitized intradermally with 100 μg OVA adsorbed on 1.6 mg alum hydroxide in 300 μL saline. Mice were challenged intraperitoneally with 30 μg OVA in 300 μL saline on day 11, and then sacrificed either 45 min or 48 hrs later for mediator analysis and eosinophil quantification, respectively. The peritoneal cavity was washed with 5 mL of Tyrode's gelatin buffer without calcium. The peritoneal lavage fluid was centrifuged [150×g, 5 min], and cell pellets were resuspended in 2 mL of Tyrode's gelatin buffer for mediator analysis and eosinophil quantification. In all experiments anti-LMIR1 was administered [1-20 μg/mouse, intraperitoneally] 30 min prior to allergen challenge. All experimental protocols were approved by the Animal Experimentation Committee of The Hebrew University of Jerusalem.

The allergic peritonitis model for testing the bi-specific antibody involved challenging the mice, at day 11, with 30 μg ovalbumin in 300 μL saline intraperitoneally. 30 min prior to challenge, BsAbs [LE1 or control, 3 μg in 100 μL saline] were injected contralaterally. Mice were sacrificed by inhaled isoflurane 45 min or 48 hr following the challenge for mediator analysis or eosinophil count, respectively. The lavage fluid was assessed for tryptase as described. For eosinophil counts, lavage fluid was centrifuged, cell numbers were normalized and cells were stained using FITC-conjugated anti-mouse CCR3 and PE-conjugated anti-mouse CD48, and finally analyzed by FACS.

Passive cutaneous anaphylaxis was generated as described [Fung-Leung et al. (1996) *J. Exp. Med.* 183:49-56] with slight modifications. Briefly, 8-10 week-old healthy female BALB/C mice were injected subcutaneously with saline or IgE anti-dinitrophenol [clone SPE7, 0.5 μg in 25 μL saline] at 4 dorsal sites. Simultaneously, BsAbs [LE1 or control, 3 μg in 25 μL saline] were injected at two of the IgE-sensitized sites. Two hours later, mice were challenged intravenously with 1 mg dinitrophenyl-HSA plus 0.75% Evan's blue in 200 μL saline. Cutaneous anaphylaxis was assessed visually by the dye leakage from blood vessels into the skin.

Statistical Analysis

Activation, survival and mediator release assays were performed in triplicates or quadruplicates and always at least from 3 different donors. Data are expressed as mean±S.D. Data were analyzed by ANOVA, followed by paired students' t-test [assuming equal variances] and Tukey-Kramer post-hoc.

Example 1

CBMC Express IRp60

In order to investigate the expression pattern of inhibitory receptors on human mast cells, a screening approach was employed, using a large panel of mAbs recognizing various inhibitory receptors. As shown in FIG. 1A, FACS analysis revealed that CBMC express high levels of IRp60, but not LIR1/ILT2, LIR3/ILT5, p58.1, p58.2, p70, p140 or NKG2A/CD94 [n=10]. One out of the ten donors expressed CD94 but not NKG2A. In addition, CBMC were positively stained for FcγRIIB, a known inhibitory receptor [data not shown].

In order to evaluate whether mature tissue mast cells express IRp60, HLMC were stained for IRp60 expression. As shown in FIG. 1B, HLMC express significant levels of IRp60 as well [n=3]. Next these cells were screened with different mAbs recognizing IRp60 [i.e. P192 and E59] to examine whether this expression pattern is antibody dependent. Both antibodies recognized similar levels of IRp60 on the surface of CBMC and HLMC [n=3.5 respectively, data not shown]. Since IRp60 was the only inhibitory receptor expressed on CBMC [besides FcγRIIB], the FACS data was confirmed with western blot analysis. Anti-IRp60 recognizes a ~60 kDa protein on human mast cells, as previously reported [Cantoni C, et al. (1999) id ibid.] [data not shown] [n=3].

Example 2

Eosinophil Derived MBP Down-Regulates IRp60 Expression on CBMC

The inventors next investigated the capability of various mediators, found in the allergic inflammatory milieu, to modulate IRp60 expression on CBMC. For this, CBMC were cultured for various time points in the presence of TNF-α, IL-3, IL-4, monomeric IgE, NGF and eosinophil derived MBP. With the exception of MBP, none of the mediators significantly influenced IRp60 expression. As shown in FIG. 2, MBP induced a decrease in the expression level of IRp60 starting at 12 hours reaching a significant effect after 24 hours [n=3, p<0.01]. The effect of MBP was charge-independent since poly-L-arginine at an equimolar range [25-100 nM] did not affect IRp60 expression.

Example 3

IRp60 Cross-Linking Inhibits IgE-Dependent Mediator Release from CBMC

Figure 3A:
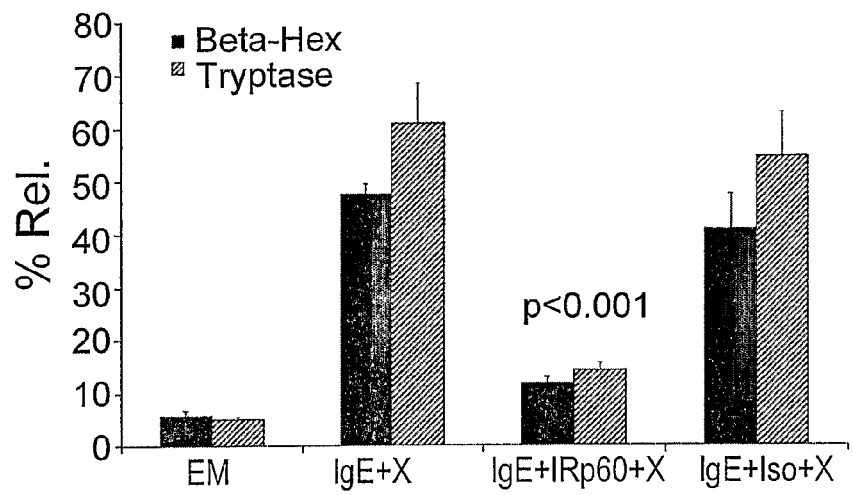
FIGS. 3A-3B: IRp60 cross-linking inhibits IgE-mediated release of FIG. 3A: Percent release of β-hexosaminidase and tryptase from IgE-activated CBMC following stimulation with anti-IRp60.
Figure 3B:
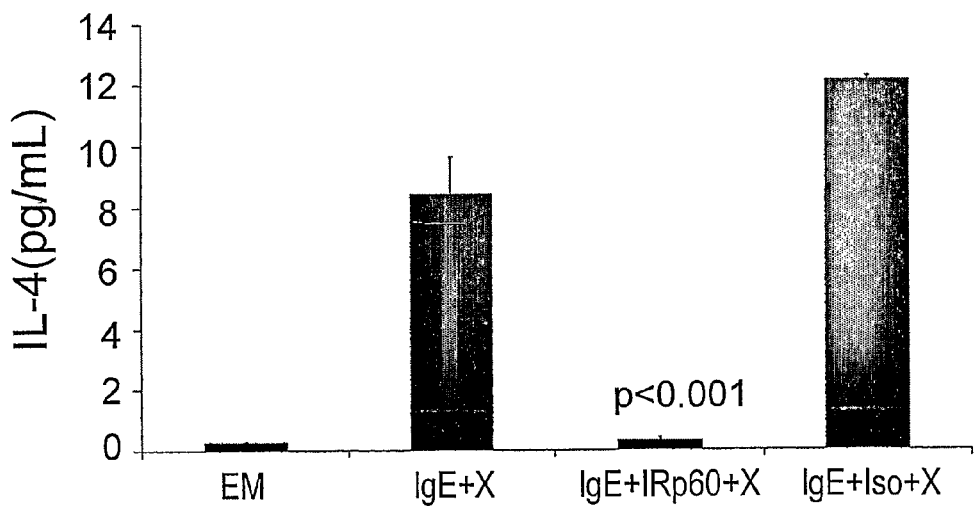

The expression of IRp60 on the surface of CBMC suggests that their responses may be regulated by this receptor. To evaluate the ability of IRp60 to inhibit CBMC degranulation, CBMC were sensitized with IgE and triggered to degranulate using an anti-IgE antibody or compound 48/80 in an anti-IRp60 coated plate. As shown in FIGS. 3A and 3B, cross-linking of IRp60 strongly and significantly inhibited IgE-mediated release of β-hexosaminidase[47.61±2.00% vs. 11.71±1.12% with anti-IRp60, p<0.001], tryptase [60.90±7.35% vs. 14.11±1.45% with anti-IRp60, p<0.001] and IL-4 [8.41±1.19 pg/mL vs. 0.32±0.09 pg/mL with anti-IRp60, p<0.001]. Interestingly, as shown in FIG. 3C, cross-linking of IRp60 did not inhibit compound 48/80-mediated release of β-hexosaminidase, tryptase and IL-4 [data not shown].

Example 4

IRp60 Cross-Linking Inhibits IgE-Induced $[Ca_{2+}]$ Influx

One of the initial steps in FcεRI dependent activation of CBMC is intracellular calcium influx. Therefore, the effect of IRp60 cross-linking on calcium influx was examined using the calcium sensor Calcium Green-1AM. As shown in FIG. 4, within 10-20 sec of anti-IgE addition a marked $[Ca_{2+}]$ increase was observed. This increase was completely abolished in response to IRp60 cross-linking [n=3].

Example 5

IRp60 Cross-Linking Inhibits SCF-Mediated CBMC Survival

SCF is by far the most important survival factor for human mast cells. SCF signaling exerts its effects upon binding to c-kit and initiating a signaling cascade that involves phosphorylation of Src-kinases and phosphatidylinositol-3-kinase. In order to examine the ability of IRp60 to interfere with c-kit signaling, CBMC were cultured in the presence or absence of SCF [100 ng/mL] in a cross-linked anti-IRp60-coated plate, followed by FACS analysis of propidium iodide [PI] positive cells. As shown in FIG. 5, IRp60 cross-linking significantly inhibited mast cell survival at both time points [10.02±0.79% and 37.68±0.69% PI+cells vs. 1.83±0.38% and 3.65±0.33% PI+cells, p<0.001 at 24 hr and 48 hr, respectively] [n=3].

Example 6

IRp60 Undergoes Tyrosine Phosphorylation and Recruits SHP-1 and SHIP-1

As mentioned above, the inhibitory effect of IRp60 on NK cells is mediated via recruitment of SHP-1 and SHP-2. In order to establish the mechanism of the inhibitory activity of IRp60 on human mast cells, CBMC were treated with sodium orthovanadate or alternatively, cross-linked, precipitated and blotted for phosphotyrosine, SHP-1,-2 and SHIP-1. As shown in FIG. 6A, upon orthovanadate pretreatment and IRp60 cross-linking, IRp60 underwent tyrosine phosphorylation. In addition, as demonstrated in FIG. 6B, IRp60 co-precipitated with SHP-1 and SHIP-1, but not with SHP-2 [n=3].

Example 7

IRp60 Regulates Mast Cells Activation and Consequent Inflammatory Response in an Allergic-Peritonitis Mouse Model In order to discern whether IRp60 has a role in regulating mast cell activation in vivo, an allergic-inflammation murine model was used. Unlike experimental asthma protocols where the role of mast cells is uncertain, the role of mast cells in murine allergic-peritonitis model has been well established [Zuany-Amorim (1994) id ibid.]. Bioinformatic analysis revealed that LMIR1 is the murine homologue of IRp60 [data not shown]. Therefore, the inventors examined whether murine mast cells express LMIR1. As shown in FIG. 7, both BMMC and peritoneal mast cells express significant levels of LMIR1. Subsequently, the regulatory effect of LMIR1 was examined by adding a neutralizing antibody recognizing this receptor. As shown in FIG. 8A, mice pretreated with anti-LMIR1 monoclonal antibody at micromolar concentrations displayed enhanced mast cell activation in response to allergen challenge and increased tryptase and β-hexosaminidase levels were measured in the peritoneal lavage fluid. In addition, as shown in FIG. 8B the resulting eosinophilic inflammation in the peritoneal lavage was augmented, and total eosinophilic inflammation was increased in comparison to Ovalbumin treated mice and ovalbumin with isotype control groups.

Example 8

IRp60 is Expressed on Human Eosinophils

In order to investigate the expression pattern of inhibitory receptors on human mast cells, a screening approach using a large panel of mAbs recognizing various inhibitory receptors was employed. As shown in FIG. 9A, FACS analysis revealed that eosinophils express high levels of IRp60, p140, LIR3/ILT5 and FcγRIIB but not LIR1/ILT2, LIR3/ILT5, p58.1, p58.2, p70, or NKG2A/CD94 (n=10). Interestingly, only 30% of the eosinophils analyzed expressed p140.

In order to evaluate whether mature tissue eosinophils express IRp60, nasal polyp eosinophils were stained for IRp60 expression. As shown in FIG. 9B, nasal polyp eosinophils express significant levels of IRp60 as well (n=3). These cells were next screened with different mAbs recognizing IRp60 (i.e. P192 and E59) to examine whether this expression pattern is antibody dependent. Both antibodies recognized similar levels of IRp60 on the surface of peripheral blood eosinophils and nasal polyp eosinophils (n=3 and 5, respectively) (data not shown).

Example 9

IRp60 Inhibits IL-5 and GM-CSF Mediated Survival of Human Eosinophils

IL-5, GM-CSF and IL-3 are important cytokines in the biology of the eosinophils and are often termed "eosinophil survival factors". In humans, upon binding to a low affinity α-chain, all three cytokines recruit a common β-chain that exerts their signaling pathways. This signaling pathway is dependent upon tyrosine phosphorylation and recruitment of Src family kinases such as Lyn and Syk. Therefore we aimed to assess whether IRp60 could modulate the anti-apoptotic effects that these cytokines transduce. For this, freshly isolated eosinophils were cross-linked with anti-IRp60 or isotype matched control and sheep-anti mouse. Thereafter, IL-5 or GM-CSF was added for at different concentrations for various time points. As shown in FIGS. 10A and 10B, IRp60 inhibited the anti-apoptotic effect of GM-CSF and IL-5 (data not shown). For example, at 18 hrs of incubation and at 50 ng/ml of GM-CSF the percentage of apoptotic cells in the untreated group was 23.16±0.65% whereas GM-CSF treated cells were only 1.25±0.23%. Cells treated with anti-IRp60 cross-linking and GM-CSF was 15.62±3.9% apoptotic. This effect was also observed at 36 hrs where GM-CSF treated cells were 13.85±0.6% apoptotic and IRp60 treated cells were 36.7±0.45% apoptotic. Interestingly the ability of IRp60 to inhibit the anti-apoptotic effect of IL-5 and GM-CSF was enhanced as the concentrations increased from 5-50 ng/ml at both time points (6.7±1.7%, 9.45±1.95%, 15.6±3.9%, 5, 20, 50 ng/ml GM-CSF respectively, 18 hrs, 19.6±0.21%, 27.5±0.63%, 36.7±0.45%, 5, 20, 50 ng/ml GM-CSF respectively, 36 hrs).

Example 10

IRp60 Inhibits IL-5 and GM-CSF Mediated Activation of Human Eosinophils

IL-5, GM-CSF and IL-3 are also able to activate eosinophils. Therefore, the inventors examined whether cross-linking of IRp60 would inhibit the activatory effect as well. As shown in FIGS. 11A and 11B, cross-linking of IRp60 completely blocked GM-CSF mediated release of IL-8 IL-1b, IL-4 and IFN-γ.

Example 11

IRp60 Inhibits Eotaxin-Dependent Chemotaxis of Human Eosinophils

One of the most important factors that regulates eosinophil trafficking into the inflamed tissue is eotaxin. Although not much is known about eotaxin signaling, several reports demonstrate that eotaxin induces tyrosine phosphorylation and recruitment of Src family kinases such as Hck and Fgr. Therefore, the inventors assessed whether IRp60 could block eotaxin-dependent activation of eosinophils. Two parameters were checked, chemotaxis and shape change.

For the chemotaxis assay (FIG. 12A), 3×10$^5$ eosinophils were incubated with anti-IRp60, anti-CCR3 or isotype (all at 5 μg/mL, 30 mins on ice) followed by sheep anti-mouse (25 μg/mL, 30 mins on ice) and washed extensively. The cells were placed in the upper chamber of a transwell plate (polycarbonate filter, 3 μm-pores, Corning Costar-Corp) in 100 μL volumes of medium, and human eotaxin (in HBSS plus 0.5% BSA) was placed in the lower chamber at 0, 1, 10, and 100 ng/mL. After incubation, cells in the lower chamber were counted by means of flow cytometry: relative cell counts were obtained by acquiring events for 60 seconds.

For the shape-change assay (FIG. 12B), 3×10$^5$ eosinophils were incubated with anti-IRp60, anti-CCR3 or isotype (all at 5 μg/mL, 30 mins on ice) followed by sheep anti-mouse (25 μg/mL, 30 mins on ice) and washed extensively. Eotaxin-induced eosinophil shape change was assessed by using gated autofluorescence/forward scatter (FSC) This assay uses differential autofluorescence to identify leukocyte types and changes in FSC to measure shape change in response to agonist. Briefly, granulocytes were isolated by means of dextran sedimentation, Percoll gradient centrifugation, and hypotonic red blood cell lysis and were preincubated for 30 minutes at 37° C. in shape-change buffer (PBS with 0.9 mmol/L CaCl$_2$, 0.5 mmol/L MgCl$_2$, 10 mmol/L glucose, 10 mmol/L HEPES, and 0.1% BSA). Cells were incubated at 37° C. in a shaking water bath, and the reaction was stopped by placing cells on ice and fixing with 600 μL of cold 4% paraformaldehyde in shape-change buffer. Cells were further analyzed by means of flow cytometry on the FACScalibur Flow Cytometer (Beckton Dickinson). Eosinophils were distinguished by their high autofluorescence in the FL2 channel (585 nm), and the FSC of 5000 cells was acquired. The percentage change in cell shape was calculated as follows: 100 x{[FSC (Chemokine)—FSC (Media)]/FSC (Media)}. Pretreatment with inhibitors did not significantly alter basal FSC.

As shown in FIGS. 12A and 12B, cross-linking of IRp60 inhibited the chemotactic responses of eosinophils that were elicited by eotaxin (FIG. 12A). In addition, IRp60 was able to completely block the eotaxin-induced shape change (FIG. 12B).

Example 12

Generation of an IgE-IRp60 BsAb

In order to monitor each step of the BsAb generation process, samples were taken following each gel filtration to assess possible material loss. Samples were run on SDS-PAGE for evaluation of the reactant Fab' fragments before the coupling, and the F(ab')2 product after coupling. As shown in FIG. 13A, native SDS-PAGE shows one of the Fab' reactants at ~50 kDa before coupling. After coupling, reducing SDS-PAGE shows the BsAb separated into two ~37 kDa heavy chain fragments and two ~25 kDa whole light chains, next to two IgG size controls. The bispecific recognition of IE1 was evaluated by FACS. As shown in FIG. 13B, IE1 recognized IgE-sensitized RBL cells similarly to anti-human IgE but not anti-human IRp60, whereas it recognized fresh human mast cells similarly to anti-human IRp60 but not anti-human IgE. The average nominal yield of the generation process was about 40%.

Example 13

Inhibition of Mast Cell Degranulation In vitro

To evaluate the potential of IE1 to inhibit mast cell activation, human mast cells sensitized with IgE were incubated with IE1 or the matching isotype control, and then activated using anti-IgE antibody. As shown in FIG. 14, IE1 inhibited almost completely the release of β-hexosaminidase from the mast cells.

Example 14

Inhibition of Allergic Responses In vivo

In order to determine whether the effect observed in isolated human mast cells in-vitro would also be observed in-vivo, a BsAb was generated termed LE1 that recognizes murine IgE and LMIR1, the murine IRp60 homologue. The LE1 or its matching isotype control were further administered to animals in two allergic response models. In allergic peritonitis, as shown in FIG. 15, LE1 completely inhibited tryptase release from degranulating peritoneal mast cells following allergen challenge. Moreover, as shown in FIGS. 16A and 16B, eosinophil counts were dramatically decreased in the groups' treated with LE1 prior to allergen challenge, meaning that fewer eosinophils were recruited to the perintoneum by the mast cells. In passive cutaneous anaphylaxis, LE1 completely inhibited dye leakage deriving from histamine and leukotriene release from skin mast cells (FIGS. 17A-17B).

The invention claimed is:

1. A bi-specific antibody comprising:
   (i) a first target recognition component which specifically binds to the inhibitory receptor IRp60; and
   (ii) a second target recognition component which specifically binds to a marker selected from the group consisting of IgE, cKIT, CCR3, IL-5R and FcεRI.

2. The bi-specific antibody of claim 1, wherein a binding of said antibody to any one of a mast cell, an eosinophil and/or a basophil inhibits allergic-type reactions.

3. The bi-specific antibody of claim 1, wherein said first and second target recognition components are linked via any one of a cross-linker, a linker compound, a carrier, a synthetic spacer, an immobilizing substrate and a $(Gly_4Ser)_3$ motif based flexible region.

4. The bi-specific antibody of claim 1, wherein said first and second target recognition components are cross-linked.

5. The bi-specific antibody of claim 1, wherein said recognition component is selected from any one of a naturally occurring, synthetic or recombinant antibody, single chain Fv (scFv), bi-functional scFv, diabody, F(ab) unit, F(ab') unit, bi-specific F(ab') conjugate, chemically cross-linked bi-functional antibody, linear antibody or a F(ab')2 antigen binding fragment of an antibody.

6. The bi-specific antibody of claim 1, wherein said recognition component is a F(ab') unit.

7. A pharmaceutical composition comprising as an active agent the bi-specific antibody of claim 1.

8. The pharmaceutical composition of claim 7, further comprising buffers, additives, stabilizers, diluents and/or excipients.

9. A method of treating an allergy, the method comprising administering to a subject in need thereof a therapeutically effective amount of a bi-specific antibody comprising:
   (i) a first target recognition component which specifically binds to the inhibitory receptor IRp60; and
   (ii) a second target recognition component which specifically binds to a marker selected from the group consisting of IgE, cKIT and CCR3;
   thereby treating the allergy.

* * * * *